(12) United States Patent
Czaplewski et al.

(10) Patent No.: US 10,301,406 B2
(45) Date of Patent: *May 28, 2019

(54) FLAME-RETARDANT ACONITIC ACID-DERIVED MONOMERS

(71) Applicant: International Business Machines Corporation, Armonk, NY (US)

(72) Inventors: Sarah K. Czaplewski, Rochester, MN (US); Brandon M. Kobilka, Tucson, AZ (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/611,423

(22) Filed: Jun. 1, 2017

(65) Prior Publication Data

US 2018/0346619 A1    Dec. 6, 2018

(51) Int. Cl.
| | |
|---|---|
| *C08K 5/521* | (2006.01) |
| *C08K 5/524* | (2006.01) |

(Continued)

(52) U.S. Cl.
CPC .............. *C08F 130/02* (2013.01); *C07F 9/12* (2013.01); *C07F 9/4015* (2013.01);
(Continued)

(58) Field of Classification Search
None
See application file for complete search history.

(56) References Cited

U.S. PATENT DOCUMENTS 2,754,319 A * 7/1956 Johnston ............... C07F 9/4006
106/18.14
2016/0251485 A1    9/2016 Boday et al.

FOREIGN PATENT DOCUMENTS

| CN | 103965245 A | 8/2014 |
| CN | 104356361 A | 2/2015 |
| GB | 1482784 A * | 8/1977 ........... H05K 3/0094 |

OTHER PUBLICATIONS

Mengal et al., "Citric acid based durable and sustainable flame retardant treatment for lyocell fabric," Carbohydrate Polymers, vol. 153, 2016, pp. 78-88, Elsevier. DOI: 10.1016/j.carbpol.2016.07.074.

(Continued)

*Primary Examiner* — Richard A Huhn
(74) *Attorney, Agent, or Firm* — Kelsey M. Skodje

(57) ABSTRACT

A flame-retardant aconitic acid-derived monomer, a process for forming a flame-retardant polymer, and an article of manufacture comprising a material that contains a flame-retardant aconitic acid-derived monomer are disclosed. The flame-retardant aconitic acid-derived monomer can have at least one phosphoryl or phosphonyl moiety with functional groups that can participate in a polymerization reaction, such as allyl, epoxy, or propylene carbonate functional groups. The process for forming the flame-retardant polymer can include forming an aconitic acid derivative, forming a phosphorus-based flame-retardant molecule, and reacting the aconitic acid derivative with the phosphorus-based flame-retardant molecule to form a flame-retardant aconitic acid-derived monomer, which is then polymerized. The aconitic acid derivative can be synthesized from aconitic acid obtained from a bio-based source. The material in the article of manufacture can be a resin or adhesive, and the article of manufacture can further comprise an electronic component.

18 Claims, 31 Drawing Sheets

(51) Int. Cl.
  *C07F 9/02* (2006.01)
  *C08F 130/02* (2006.01)
  *C08G 79/04* (2006.01)
  *C09J 9/00* (2006.01)
  *C09J 143/02* (2006.01)
  *C09J 185/02* (2006.01)
  *H05K 1/03* (2006.01)
  *H01B 3/30* (2006.01)
  *C07F 9/655* (2006.01)
  *C07F 9/12* (2006.01)
  *C07F 9/40* (2006.01)
  *C07F 9/141* (2006.01)
  *C07F 9/113* (2006.01)
  *C08K 5/00* (2006.01)
  *C07F 9/09* (2006.01)
  *C07C 69/07* (2006.01)
  *C07C 69/003* (2006.01)

(52) U.S. Cl.
  CPC .......... *C07F 9/4021* (2013.01); *C07F 9/4084* (2013.01); *C07F 9/4093* (2013.01); *C07F 9/65502* (2013.01); *C07F 9/65505* (2013.01); *C07F 9/65515* (2013.01); *C08G 79/04* (2013.01); *C09J 9/00* (2013.01); *C09J 143/02* (2013.01); *C09J 185/02* (2013.01); *H01B 3/307* (2013.01); *H05K 1/0373* (2013.01); *C07C 69/003* (2013.01); *C07C 69/07* (2013.01); *C07F 9/091* (2013.01); *C07F 9/093* (2013.01); *C07F 9/113* (2013.01); *C07F 9/1411* (2013.01); *C07F 9/1412* (2013.01); *C08K 5/0066* (2013.01); *C08K 5/521* (2013.01); *C08K 5/524* (2013.01); *C08L 2201/02* (2013.01); *C08L 2666/84* (2013.01); *C09J 2203/326* (2013.01); *H05K 1/0326* (2013.01); *H05K 2201/012* (2013.01)

(56) References Cited

OTHER PUBLICATIONS

Czaplewski et al., "Flame-Retardant Aconitic Acid-Derived Small Molecules," U.S. Appl. No. 15/611,237, filed Jun. 1, 2017.
Czaplewski et al., "Functionalized Flame-Retardant Aconitic Acid-Derived Molecules," U.S. Appl. No. 15/611,313, filed Jun. 1, 2017.
Czaplewski et al., "Flame-Retardant Aconitic Acid-Derived Cross-Linkers," U.S. Appl. No. 15/611,360, filed Jun. 1, 2017.
List of IBM Patents or Patent Applications Treated as Related, Signed Jun. 1, 2017, 2 pages.
"Poly Star UM 55", Poly vinyl chloride / Vinyl Acetate copolymer, Data Sheet, retrieved from kianresin.com, Sep. 2018, 2 pages.
Meyer et al., "The synthesis of citric acid phosphate," Journal of the American Chemical Society, 1959, 81, pp. 2094-2096 (Abstract Only).

* cited by examiner

PG = TMS, TES, TPS, TIPS, MOM, THP

FLAME-RETARDANT ACONITIC ACID-DERIVED MONOMERS

BACKGROUND

The present disclosure relates to bio-renewable flame-retardant compounds and, more specifically, flame-retardant aconitic acid-derived monomers.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Aconitic acid (propene-1,2,3-tricarboxylic acid) is one example of a bio-based compound that can have applications as a component of various polymers, resins, and small molecules. Aconitic acid is an intermediate in the citric acid cycle, wherein it is acted upon by the aconitase enzyme. Bio-based materials, such as sugarcane or citric acid, are common sources of aconitic acid.

SUMMARY

Various embodiments are directed to flame-retardant aconitic acid-derived monomers. The flame-retardant aconitic acid-derived monomers can have at least one phosphoryl or phosphonyl moiety with at least one functional group selected from a group consisting of an allyl functional group, an epoxy functional group, and a propylene carbonate functional group. The flame-retardant aconitic acid-derived monomers can be synthesized from mono-functionalized, di-functionalized, or tri-functionalized aconitic acid derivatives. The flame-retardant aconitic acid-derived monomers can be starting material in the synthesis of flame-retardant polymers. Additional embodiments are directed to forming a flame-retardant polymer. The flame-retardant polymer can be produced by forming an aconitic acid derivative, forming a phosphorus-based flame-retardant molecule, and reacting the aconitic acid derivative and the phosphorus-based flame-retardant molecule to form a flame-retardant aconitic acid-derived monomer. The flame-retardant aconitic acid-derived monomer can then be polymerized, forming the flame-retardant polymer. The aconitic acid derivative can be carboxysuccinic acid, 2-(hydroxymethyl)-1,4-butenediol, or 2-(hydroxymethyl)-1,4-butanediol, and can be synthesized from aconitic acid obtained from a bio-based source. The phosphorus-based flame-retardant molecule can be a phosphate-based molecule or a phosphonate-based molecule with an allyl functional group or an epoxy functional group. The flame-retardant aconitic acid-derived monomer can be reacted further to form a propylene carbonate functional group. The polymerization of the flame-retardant aconitic acid-derived monomer can involve a basic reagent, a second monomer with at least two hydroxyl groups, a second monomer with at least two amino groups, or a Ziegler-Natta catalyst. Further embodiments are directed to an article of manufacture comprising a material that contains a flame-retardant aconitic acid-derived monomer. The material can be a resin, plastic, or adhesive. The article of manufacture can also comprise a printed circuit board.

DETAILED DESCRIPTION

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can be found in fermentation technologies, membrane technologies, and genetic engineering. Two approaches that can use biotechnologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant molecules or cross-linkers can be incorporated into polymers. Additionally, flame-retardant monomers can be polymerized to form flame-retardant polymers.

Aconitic acid (propene-1,2,3-tricarboxylic acid) is one example of a bio-based compound that can have applications as a component of various polymers, resins, and monomers. Aconitic acid is an intermediate in the conversion of citrate to isocitrate during the citric acid cycle. On an industrial scale, aconitic acid is commonly obtained from fermented sugarcane extract, or synthesized from citric acid. It can be obtained from the plant- and microorganism-based biosources discussed above, or synthesized from petroleum-based raw materials. According to some embodiments of the present disclosure, aconitic acid is used as a precursor for flame-retardant monomers. The aconitic acid-based flame-retardant monomers can be added to polymers, fabrics, resins, or other materials during blending, curing, foaming, extrusion, or other processing techniques. In addition to directly adding the aconitic acid-based flame-retardant monomers to the materials during processing, the added aconitic acid-based flame-retardant monomers can be contained within microcapsules.

Figure 1:
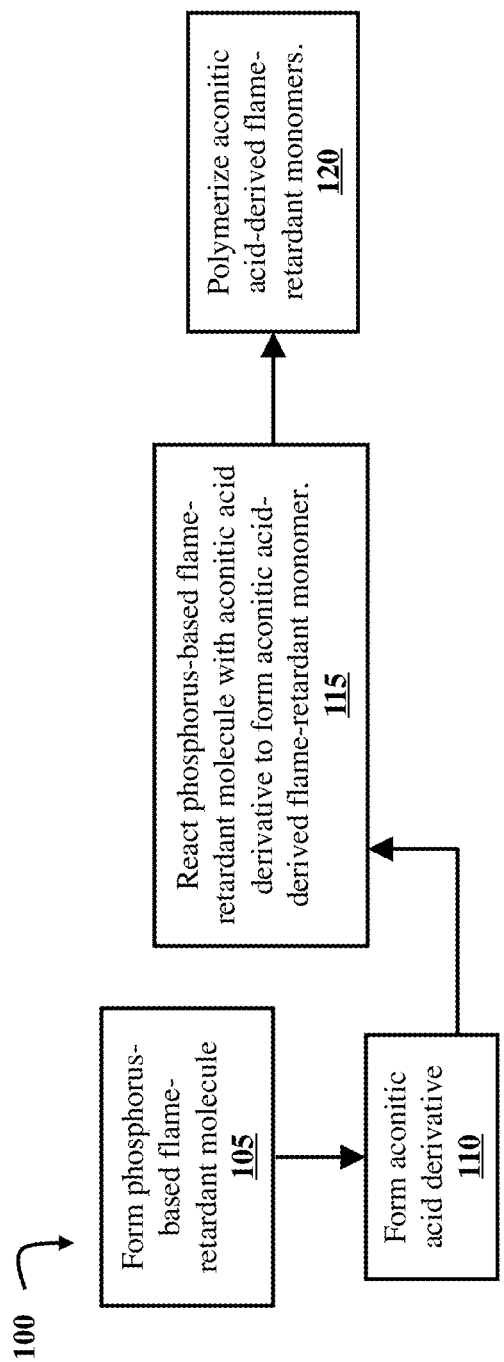
FIG. 1 is a flow diagram illustrating a process of forming a flame-retardant polymer containing an aconitic acid-based flame-retardant monomer, according to some embodiments of the present disclosure.

FIG. 1 is a flow diagram illustrating a process 100 of forming a flame-retardant polymer containing an aconitic acid-based flame-retardant monomer, according to some embodiments of the present disclosure. Process 100 begins with the formation of a phosphorus-based flame-retardant molecule. This is illustrated at step 105. The phosphorus-based flame-retardant molecule has either a phosphoryl or a phosphonyl moiety (collectively referred to as an FR group) with an attached R functional group or phenyl (Ph) group. The R groups that are attached to the FR groups can vary, as is discussed in greater detail below. The phosphorus-based flame-retardant molecules can be phosphate- or phosphonate-based flame-retardant molecules. The structures and syntheses of phosphorus-based flame-retardant molecules are discussed in greater detail with regard to FIGS. 2A-3D.

Process 100 continues with the formation of an aconitic acid derivative. This is illustrated at step 110. The derivatives can have one, two, or three hydroxyl groups to which phosphorus-based flame-retardant molecules with allyl or epoxy functional groups can be bound. Examples of aconitic acid derivatives are discussed in greater detail with regard to FIGS. 4A-4G. It should be noted that the formation of the aconitic derivative in step 110 is illustrated as occurring after the formation of the phosphorus-based flame-retardant molecule in step 105. However, in some embodiments, step 110 can occur before step 105.

The aconitic acid derivative and the phosphorus-based flame-retardant molecule are chemically reacted in order to form an aconitic acid-based flame-retardant monomer. This is illustrated at step 115. The identity of the aconitic acid-derived flame retardant monomer is determined by the aconitic acid derivative and the phosphorus-based flame-retardant molecule used in the reaction. The phosphorus-based flame-retardant molecules react with hydroxyl groups on the aconitic acid derivatives to provide the FR group with an attached R group. Examples of R groups can include allyl groups, epoxy groups, and propylene carbonate groups. The syntheses and structures of aconitic acid-based flame-retardant monomers are discussed in greater detail with regard to FIGS. 5A-5F.

The aconitic acid-based flame-retardant monomer formed in step 115 is polymerized, yielding a flame-retardant aconitic acid-based polymer. This is illustrated at step 120. The flame-retardant aconitic acid-derived monomer can be polymerized in a reaction with a base and/or a second monomer. Additionally, in some embodiments, the flame-retardant aconitic acid-derived monomer can be polymerized in a reaction with a Ziegler-Natta catalyst. Polymerizations reactions with the flame-retardant aconitic acid-derived monomer are discussed in greater detail with regard to FIG. 8B.

Figure 2A:
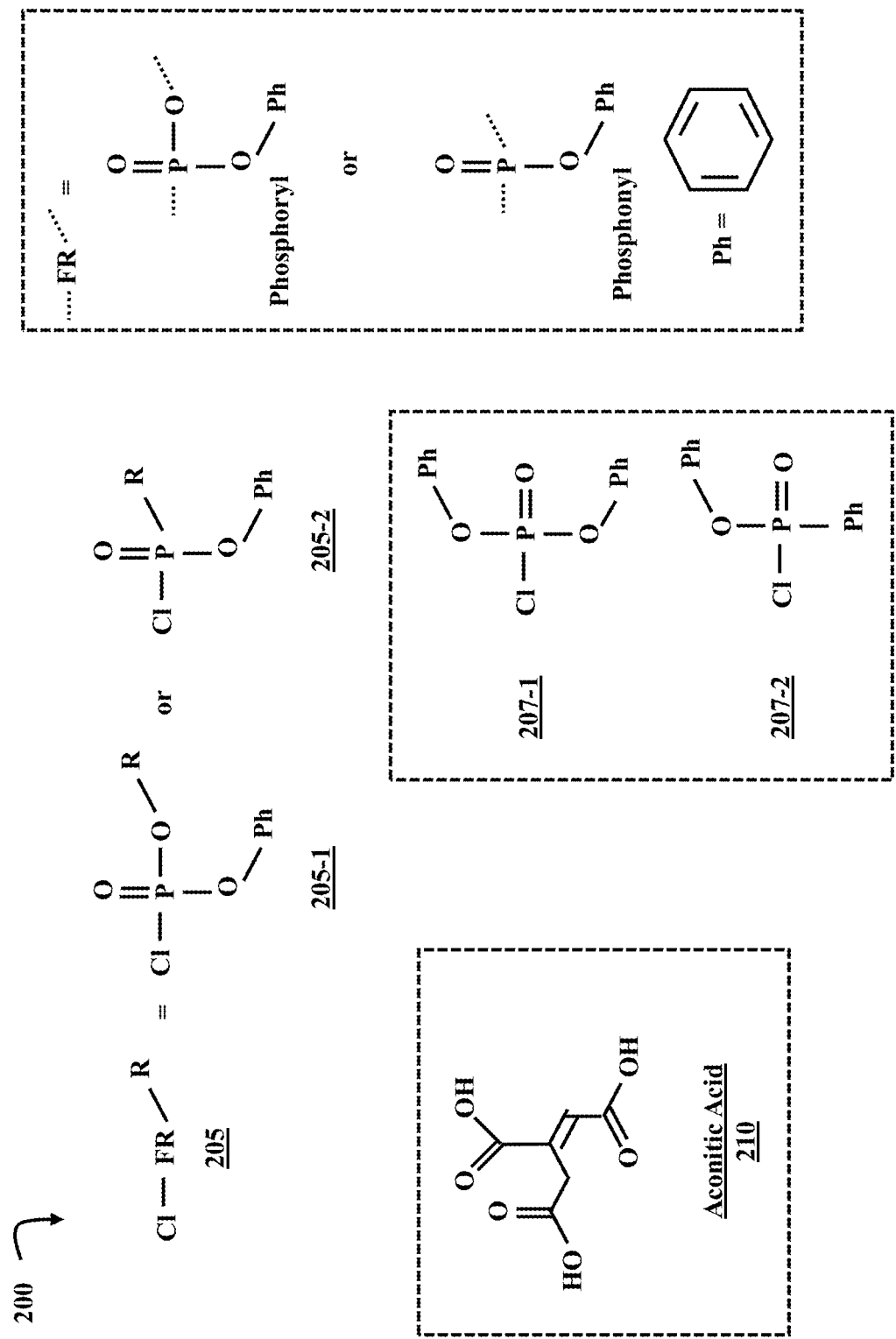
FIG. 2A is a diagrammatic representation of the molecular structures of R-functionalized phosphorus-based flame-retardant molecules, phenyl-substituted flame retardant phosphorus-based flame-retardant molecules, and aconitic acid, according to some embodiments of the present disclosure.

FIG. 2A is a diagrammatic representation of the molecular structures 200 of R-functionalized phosphorus-based flame-retardant molecules 205-1 and 205-2 (referred to collectively as 205), phenyl-substituted phosphorus-based flame-retardant molecules 207-1 and 207-2 (referred to collectively as 207), and aconitic acid 210, according to some embodiments of the present disclosure. Each phosphorus-based flame-retardant molecule is either a phosphate-based flame-retardant molecule 205-1 and 207-1 or phosphonate-based flame-retardant molecule 205-2 and 207-2. Herein, phosphoryl and phosphonyl moieties are replaced by the abbreviation "FR" in order to simplify illustrations of the molecular structures.

The phenyl-substituted flame-retardant phosphorus-based flame-retardant molecules 207-1 and 207-2, each have two phenyl (Ph) substituents. Each R-functionalized phosphorus-based flame-retardant molecule 205 has a phenyl (Ph) substituent in addition to its R functional group. Examples of R functional groups are discussed in greater detail with regard to FIG. 2B. In some embodiments, one or more phenyl groups on a phosphorus-based flame-retardant molecule 205 or 207 are replaced by another alkyl substituent (e.g., ethyl, methyl, propyl, isopropyl, etc.). Prophetic syntheses of the R-functionalized phosphorus-based flame-retardant molecules 205 are discussed with regard to FIGS. 3A and 3B. The phosphorus-based flame-retardant molecules 205 and 207 are reacted with the aconitic acid derivatives to form aconitic acid-based flame-retardant monomers.

Figure 2B:
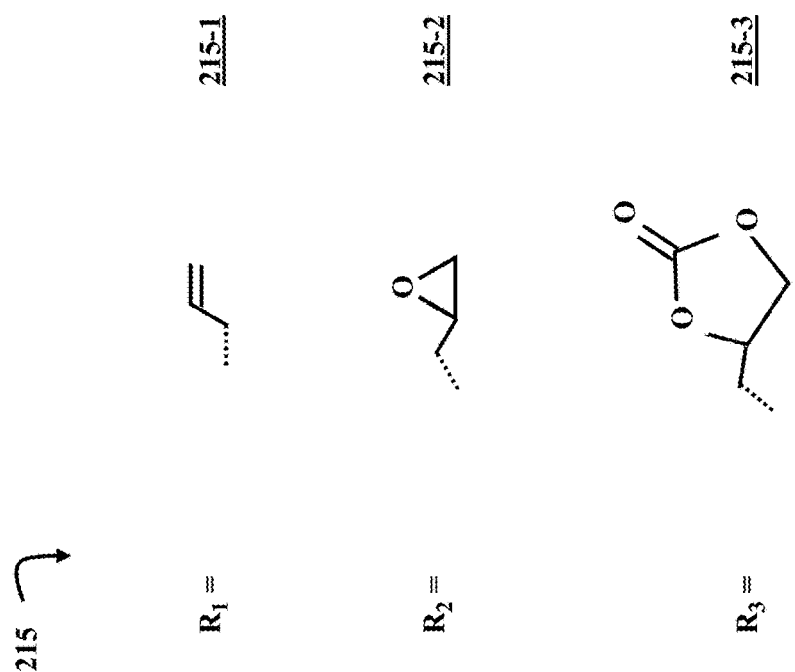
FIG. 2B is a diagrammatic representation of functional R groups, according to some embodiments of the present disclosure.

FIG. 2B is a diagrammatic representation of R functional groups 215, according to some embodiments of the present disclosure. These R groups, $R_1$ 215-1, $R_2$ 215-2, and $R_3$ 215-3, are functional groups that can optionally be bound to the flame-retardant aconitic acid-derived monomers. $R_1$ 215-1 is an allyl functional group, $R_2$ 215-2 is an epoxy functional group, and $R_3$ 215-3 is a propylene carbonate functional group. The R groups are reactive in the polymerization reactions, which are discussed in greater detail with regard to FIG. 8B. In some embodiments, the R groups are replaced by phenyl (Ph) groups, which do not participate in the polymerization reactions.

Figure 3A:
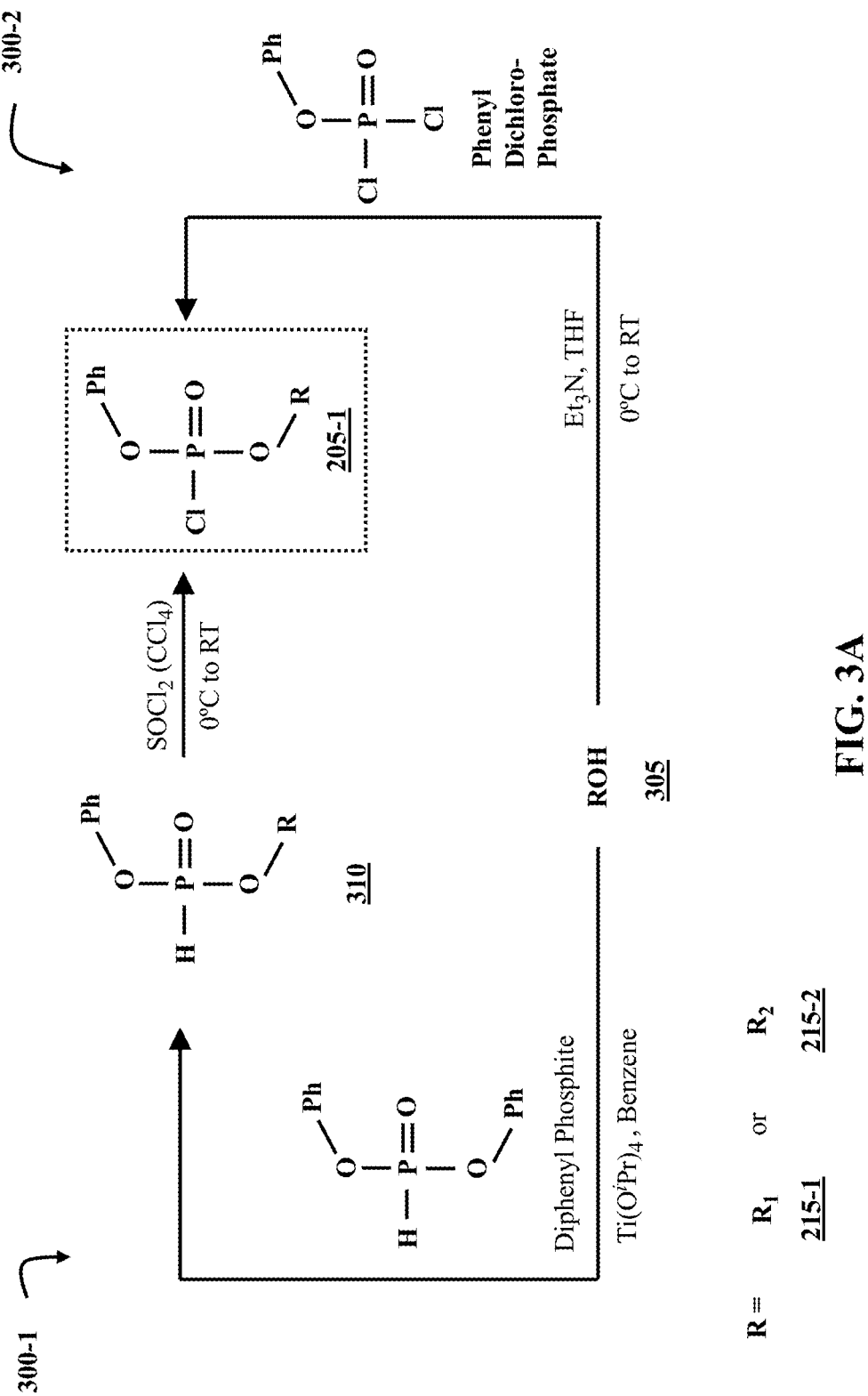
FIG. 3A is a chemical reaction diagram illustrating two processes of synthesizing an R-functionalized phosphate-based flame-retardant molecule, according to some embodiments of the present disclosure.

FIG. 3A is a chemical reaction diagram illustrating two processes 300-1 and 300-2 of synthesizing the R-functionalized phosphate-based flame-retardant molecule 205-1, according to some embodiments of the present disclosure. In both processes 300-1 and 300-2, an alcohol 305 is a starting material for the R-functionalized phosphate-based flame-retardant molecule 205-1. The alcohol 305 has either an allyl R group 215-1 or an epoxy R group 215-2. It should be noted that, though an allyl group 215-1 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphonate and titanium isopropoxide (Ti(O$^i$Pr)$_4$) in benzene to produce a precursor 310 to the R-functionalized phosphate-based flame-retardant molecule 205-1. In this pseudo-transesterification reaction, the precursor 310 is formed when a phenyl (Ph) substituent on diphenyl phosphite is replaced by the R group from the alcohol 305. The precursor 310 is then reacted with thionyl chloride (SOCl$_2$) and carbon tetrachloride (CCl$_4$) over a range of 0° C. to room temperature (RT, e.g., 15-25° C.), forming the R-functionalized phosphate-based flame-retardant molecule 205-1. In process 300-2, the alcohol 305 is reacted with phenyl dichlorophosphate in a tetrahydrofuran (THF) solution containing triethyl amine (Et$_3$N). This process is carried out over a range of 0° C. to room temperature (RT, e.g., 15-25° C.). A chloride on the phenyl dichlorophosphate is replaced by the alcohol 305, forming the R-functionalized phosphate-based flame-retardant molecule 205-1.

Figure 3B:
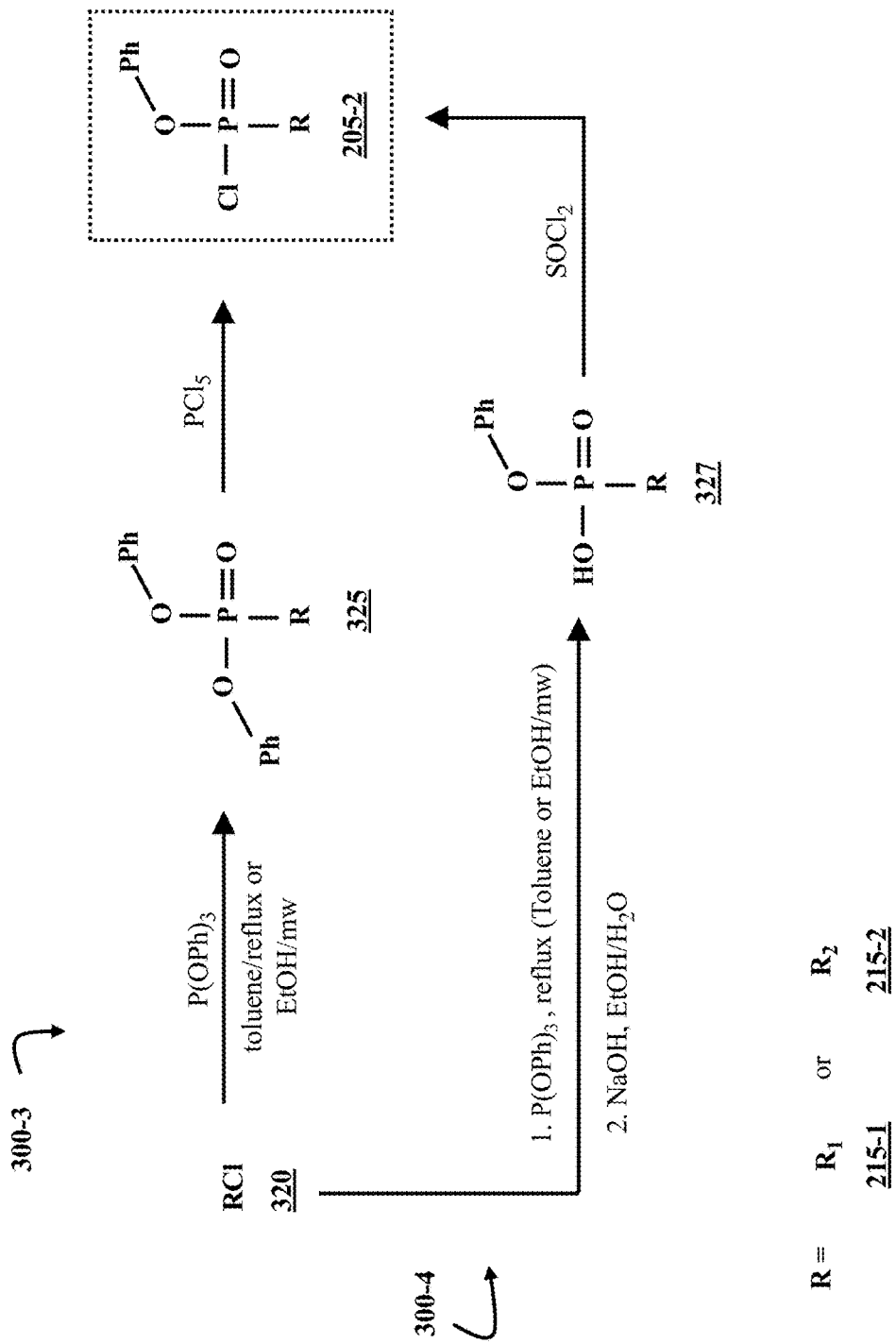
FIG. 3B is a chemical reaction diagram illustrating two processes of synthesizing an R-functionalized phosphonate-based flame-retardant molecule, according to some embodiments of the present disclosure.

FIG. 3B is a chemical reaction diagram illustrating two processes 300-3 and 300-4 of synthesizing the R-functionalized phosphonate-based flame-retardant molecule 205-2, according to some embodiments of the present disclosure. In both processes 300-3 and 300-4, an organochloride 320 is a starting material for the R-functionalized phosphonate-based flame-retardant molecule 205-2. The organochloride has either an allyl R group 215-1 or an epoxy R group 215-2. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite (P(OPh)$_3$). The mixture is heated, either by refluxing in toluene or microwaving (mw) in ethanol (EtOH), producing a phosphonyl ester precursor 325 to the R-functionalized phosphonate-based flame-retardant molecule 205-2. The phosphonyl ester precursor 325 is reacted with phosphorus pentachloride (PCl$_5$) to form the R-functionalized phosphonate-based flame-retardant molecule 205-2.

In process 300-4, a mixture of the organochloride 320 and triphenyl phosphite (P(OPh)$_3$) is heated, either by refluxing in toluene or microwaving (mw) in ethanol (EtOH), forming a phenylphosphinic acid precursor 327 to the R-functionalized phosphonate-based flame-retardant molecule 205-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the R-functionalized phosphonate-based flame-retardant molecule 205-2.

Figure 4A:
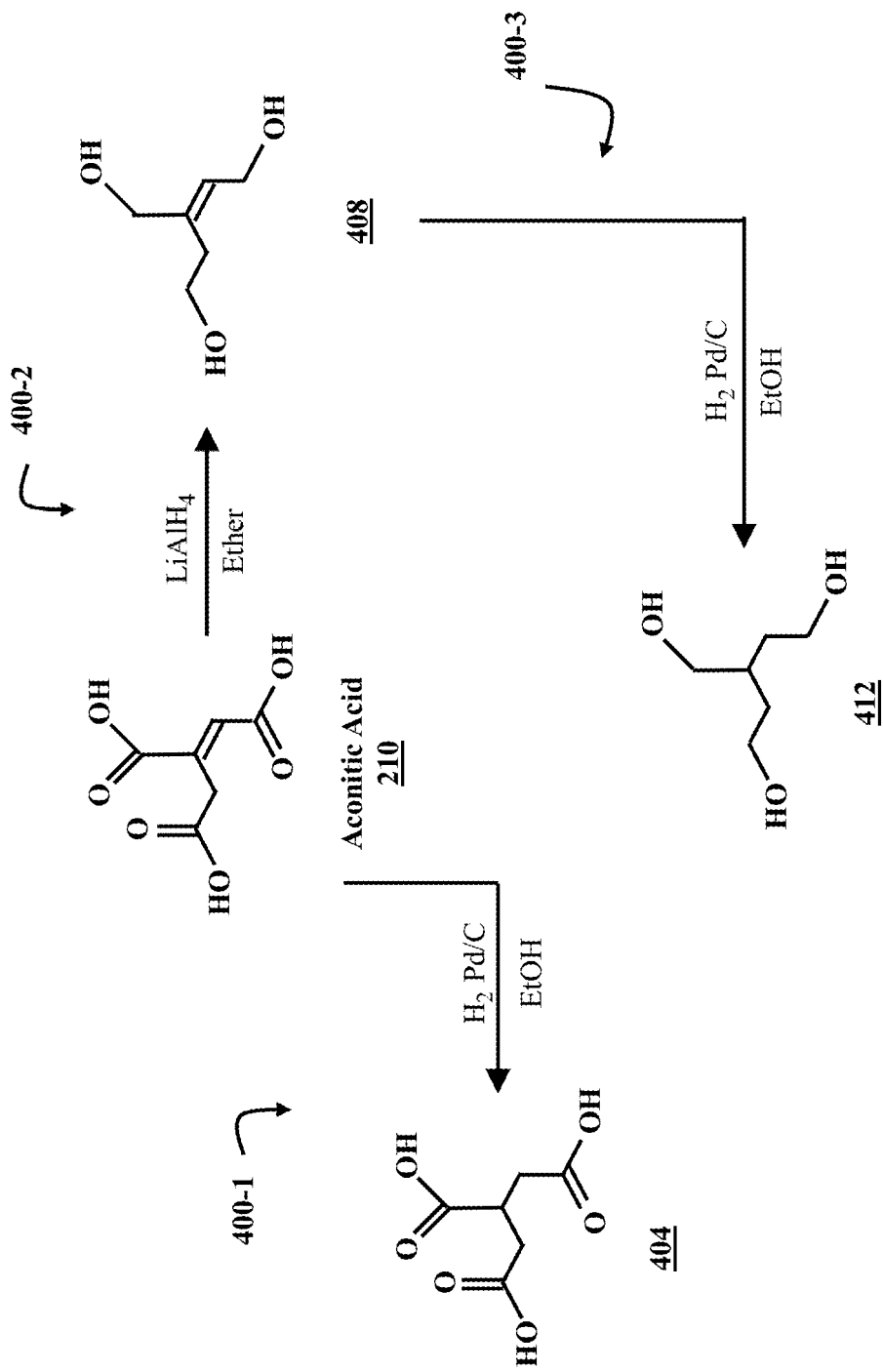
FIG. 4A is chemical reaction diagram illustrating processes of synthesizing tri-hydroxyl aconitic acid derivatives, according to some embodiments of the present disclosure.

FIG. 4A is chemical reaction diagram illustrating processes 400-1, 400-2, and 400-3 of synthesizing tri-hydroxyl aconitic acid derivatives, according to some embodiments of the present disclosure. The three tri-hydroxyl aconitic acid derivatives are carboxysuccinic acid 404, a butenetriol 408 (2-(hydroxymethyl)-1,4-butenediol), and a butanetriol 412 (2-(hydroxymethyl)-1,4-butanediol). The derivatives each have three hydroxyl groups, and are precursors for tri-functionalized flame-retardant aconitic acid-derived monomers, as is described in greater detail with regard to FIGS. 5A-5F.

In process 400-1, aconitic acid 210 is reduced in an ethanol solution. The reduction is carried out with hydrogen gas ($H_2$) and a palladium on carbon (Pd/C) catalyst, producing carboxysuccinic acid 410. In process 400-2, aconitic acid 210 is reduced by lithium aluminum hydride ($LiAlH_4$) in ether ($Et_2O$), producing the butenetriol 408. In process 400-3, butenetriol 408 is reduced under the same conditions as aconitic acid 210 in process 400-1, producing the butanetriol 412. Though FIG. 4A illustrates processes 400-1, 400-2, and 400-3 as involving the reducing agents $LiAlH_4$ and $H_2$ with Pd/C, other reducing agents can be used (e.g., sodium borohydride ($NaBH_4$), carbon monoxide (CO), iron (II) compounds, etc.). In addition, in some embodiments, carboxysuccinic acid, butenetriol, and butanetriol are obtained from commercial sources.

Figure 4B:
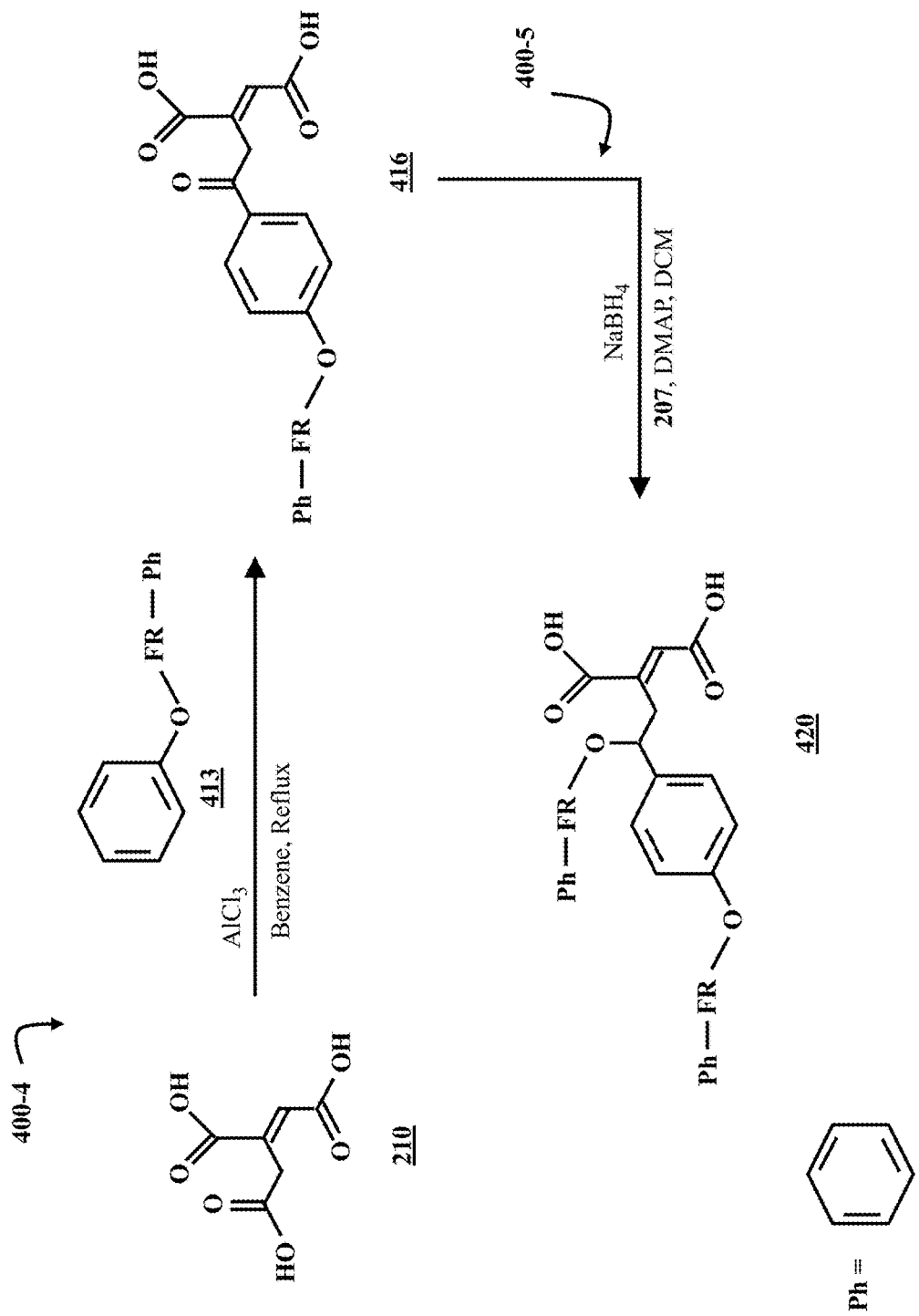
FIG. 4B is a chemical reaction diagram illustrating processes of synthesizing two FR-substituted aconitic acid derivatives, according to some embodiments of the present disclosure.

FIG. 4B is a chemical reaction diagram illustrating processes 400-4 and 400-5 of synthesizing two Ph-FR-substituted aconitic acid derivatives, according to some embodiments of the present disclosure. The two derivatives are a mono-Ph-FR aconitic acid derivative 416 and a di-Ph-FR aconitic acid derivative 420. The mono-Ph-FR derivative has a single phenyl (Ph)-substituted FR (phosphoryl or phosphonyl) moiety, and the di-Ph-FR derivative has two phenyl (Ph)-substituted FR groups. These derivatives 416 and 420 each have two hydroxyl functional groups, and are precursors for di-functionalized flame-retardant aconitic acid derivatives.

Process 400-4 is a Friedel-Crafts acylation reaction targeting the carboxylic acid moiety bonded to the aliphatic portion of the aconitic acid 210 molecule. In this prophetic example, aconitic acid 210 is combined with a phenyl-substituted flame-retardant phenol compound 413 and aluminum chloride ($AlCl_3$) in a benzene solution. The reaction mixture is refluxed, producing the mono-Ph-FR aconitic acid derivative 416. The phenyl-substituted flame-retardant phenol compound 413 is synthesized by reacting phenol and a phenyl-substituted phosphorus-based flame-retardant molecule 207 with catalytic dimethylaminopyridine (DMAP) in a dichloromethane (DCM) solution. In process 400-5, the ketone moiety on the mono-Ph-FR aconitic acid derivative 416 is reduced by sodium borohydride ($NaBH_4$). A subsequent reaction with a phenyl-substituted phosphorus-based flame-retardant molecule 207 and catalytic DMAP in a DCM solution produces the di-Ph-FR aconitic acid derivative 420.

Figure 4C:
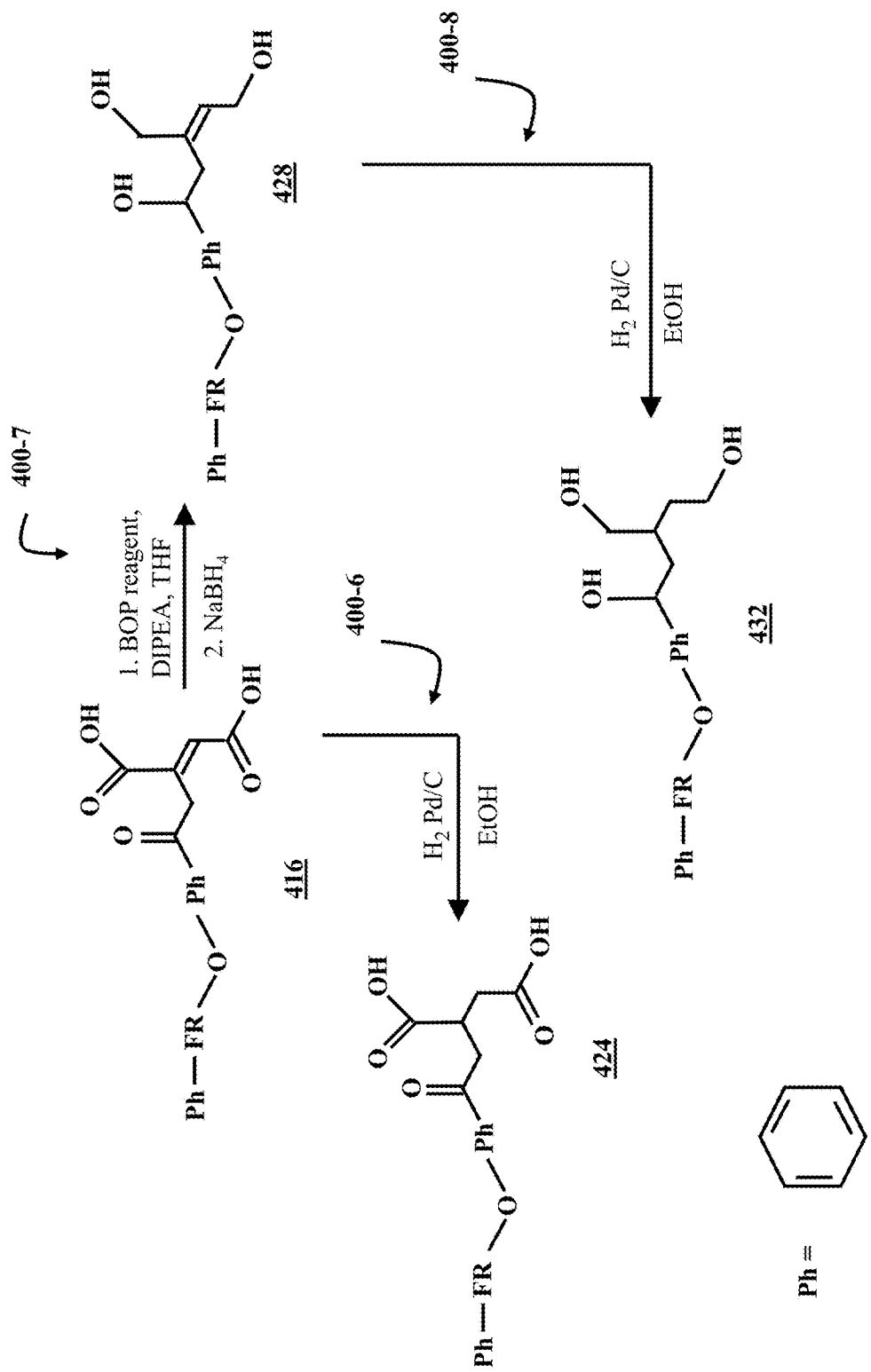
FIG. 4C is a chemical reaction diagram illustrating processes of synthesizing derivatives of a mono-Ph-FR aconitic acid derivative, according to some embodiments of the present disclosure.

FIG. 4C is a chemical reaction diagram illustrating processes 400-6, 400-7, and 400-8 of synthesizing derivatives of the mono-Ph-FR aconitic acid derivative 416, according to some embodiments of the present disclosure. Each derivative has a single phenyl (Ph)-substituted phosphoryl or phosphonyl (FR) moiety. The derivatives are a mono-Ph-FR carboxysuccinic acid derivative 424, a mono-Ph-FR butenetriol derivative 428, and a mono-Ph-FR butanetriol derivative 432. These derivatives are precursors for di- and tri-functionalized flame-retardant aconitic acid-derived monomers. The syntheses and structures of the di- and tri-functionalized flame-retardant aconitic acid-derived monomers formed from derivatives 424, 428, and 432 are illustrated in FIGS. 5E, 5F, and 6B, respectively.

In process 400-6, the mono-Ph-FR aconitic acid derivative 416 is reduced in an ethanol solution. The reduction is carried out with hydrogen gas ($H_2$) and a palladium on carbon (Pd/C) catalyst and produces the mono-Ph-FR carboxysuccinic acid derivative 424. In process 400-7, the mono-Ph-FR aconitic acid derivative 416 is reduced by (Benzotriazol-1-yloxy) tris-(dimethylamino) phosphonium hexafluorophosphate (BOP reagent) with N,N-diisopropylethylamine (DIPEA) in a tetrahydrofuran (THF) solution. This reduction produces the mono-Ph-FR butenetriol derivative 428. In process 400-8, the mono-Ph-FR butenetriol derivative 428 is reduced under reaction conditions that are substantially the same as the reaction conditions of process 400-6. The reduction of the mono-Ph-FR butenetriol derivative 428 produces the mono-Ph-FR butanetriol derivative 432.

Figure 4D:
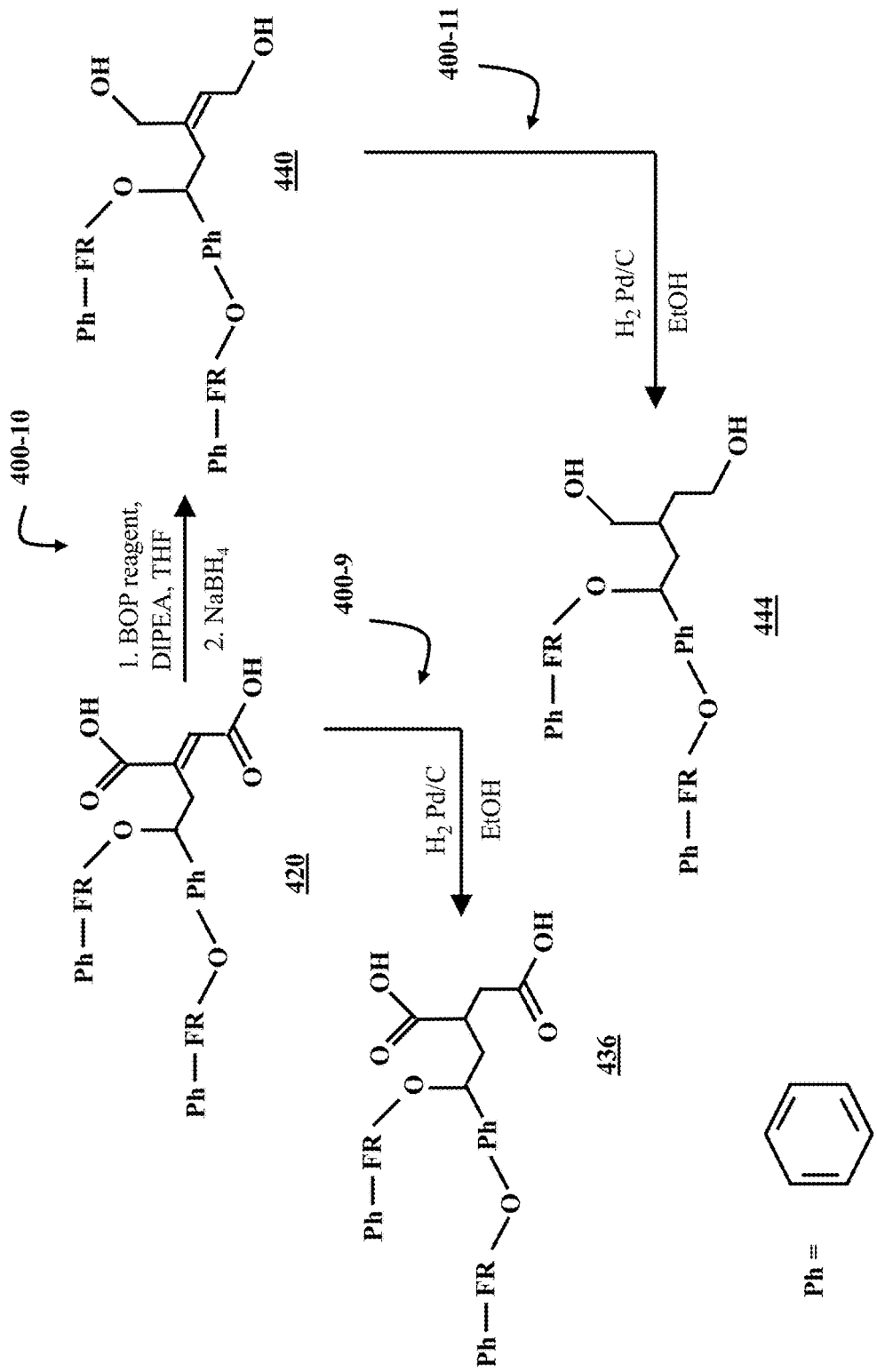
FIG. 4D is a chemical reaction diagram illustrating processes of synthesizing derivatives of a di-Ph-FR aconitic acid derivative, according to some embodiments of the present disclosure.

FIG. 4D is a chemical reaction diagram illustrating processes 400-9, 400-10, and 400-11 of synthesizing derivatives of the di-Ph-FR aconitic acid derivative 420, according to some embodiments of the present disclosure. Each derivative can have two phenyl (Ph)-substituted phosphoryl or phosphonyl (FR) moieties. However, in some embodiments, the di-Ph-FR aconitic acid derivatives can have both a phosphoryl and a phosphonyl (FR) moiety. The identity of the FR moiety is determined by the identity of the phosphorus-based flame-retardant molecule 205 or 207 used in the synthesis. The derivatives are a di-Ph-FR carboxysuccinic acid derivative 436, a di-Ph-FR butenetriol derivative 440, and a di-Ph-FR butanetriol derivative 444. These derivatives are precursors for di- and tri-functionalized flame-retardant aconitic acid-derived monomers. The syntheses and structures of the di- and tri-functionalized flame-retardant aconitic acid-derived monomers formed from derivatives 436, 440, and 444 are illustrated in FIGS. 6D, 6E, and 6F, respectively.

In process 400-9, the di-Ph-FR aconitic acid derivative 420 is reduced in an ethanol solution. The reduction is carried out with hydrogen gas ($H_2$) and a palladium on carbon (Pd/C) catalyst, and produces the di-Ph-FR carboxysuccinic acid derivative 436. In process 400-10, the di-Ph-FR aconitic acid derivative 436 is reduced by (Benzotriazol-1-yloxy) tris-(dimethylamino) phosphonium hexafluorophosphate (BOP reagent) with N,N-diisopropylethylamine (DIPEA) in a tetrahydrofuran (THF) solution. This reduction produces the di-Ph-FR butenetriol derivative 440. In process 400-11, the di-Ph-FR butenetriol derivative 440 is reduced under reaction conditions that are substantially the same as the reaction conditions of process 400-9. The reduction of the di-Ph-FR butenetriol derivative 440 produces the di-Ph-FR butanetriol derivative 444.

Figure 4E:
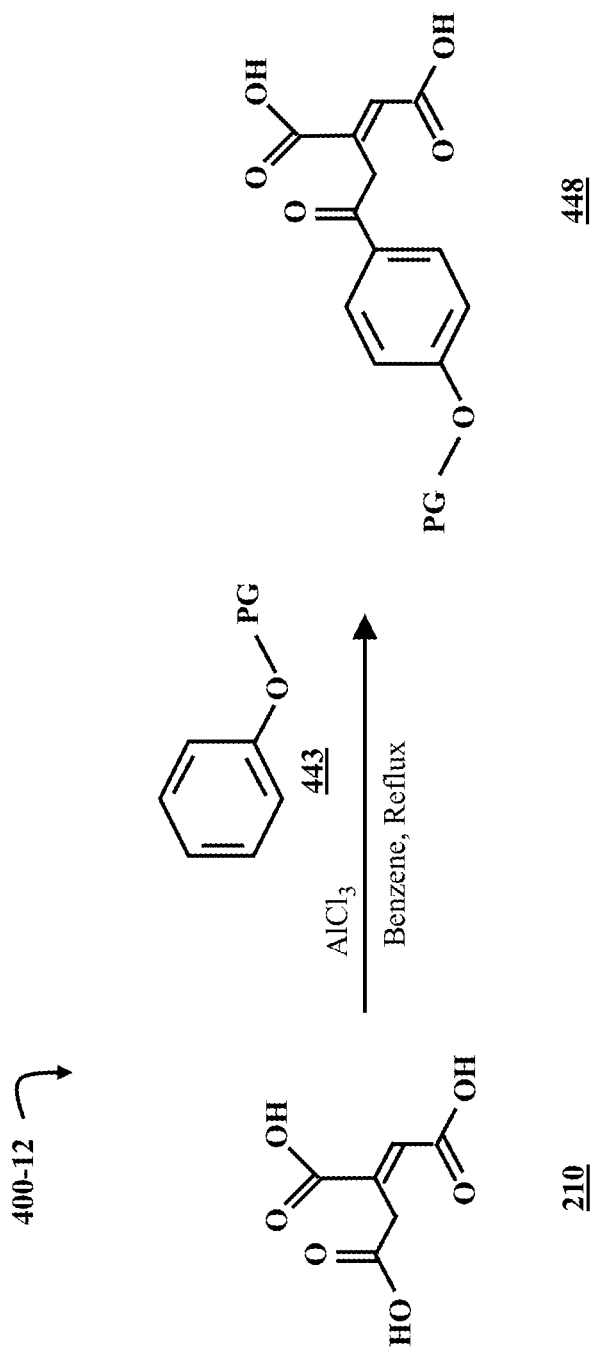
FIG. 4E is a chemical reaction diagram illustrating a process of synthesizing a protected phenol-substituted aconitic acid derivative, according to some embodiments of the present disclosure.

FIG. 4E is a chemical reaction diagram illustrating a process 400-12 of synthesizing a protected phenol-substituted aconitic acid derivative 448, according to some embodiments of the present disclosure. Process 400-12 is a Friedel-Crafts acylation reaction targeting the carboxylic acid moiety bonded to the aliphatic portion of the aconitic acid 210 molecule. In this prophetic example, aconitic acid 210 is combined with a protected phenol (PG-phenol) 443 and aluminum chloride ($AlCl_3$) in a benzene solution. The reaction mixture is refluxed, producing the PG-phenol-substituted aconitic acid derivative 448. The protecting group (PG) on the PG-phenol 443 can vary. Examples of protecting groups can include trimethylsilyl (TMS), triethylsilyl (TES), tert-butyldiphenylsilyl (TBS), triisopropylsilyl (TIPS), methoxymethyl ether (MOM), and tetrahydropyranyl (THP) groups.

Figure 4F:
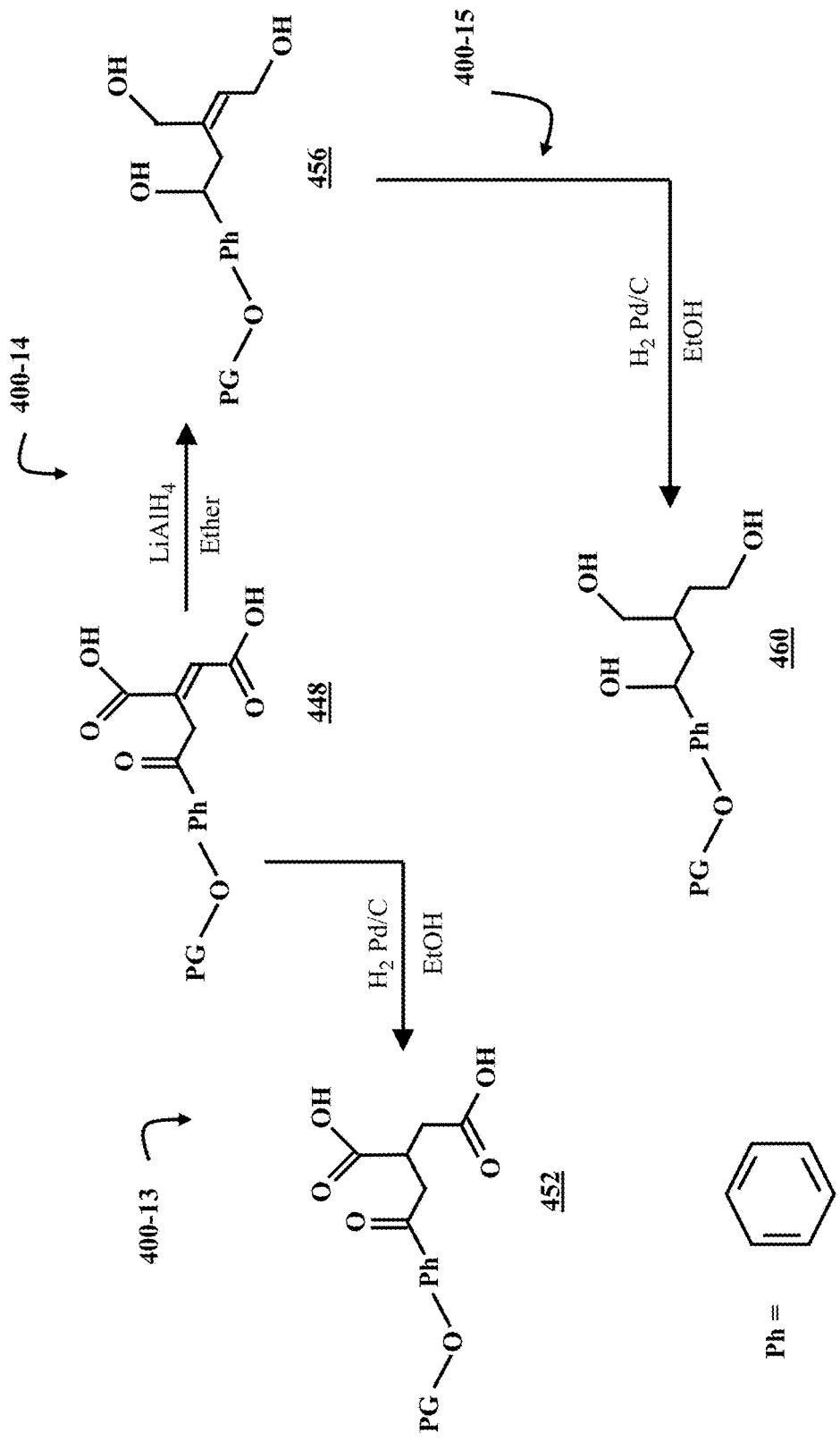
FIG. 4F is a chemical reaction diagram illustrating processes of forming derivatives of the protected phenol-substituted aconitic acid derivative, according to some embodiments of the present disclosure.

FIG. 4F is a chemical reaction diagram illustrating processes 400-13, 40-14, and 400-15 of forming derivatives of the PG-phenol-substituted aconitic acid derivative 448, according to some embodiments of the present disclosure. The derivatives are a PG-phenol-substituted carboxysuccinic acid derivative 452, a PG-phenol-substituted butenetriol derivative 456, and a PG-phenol-substituted butanetriol derivative 460. Each of these processes is a reduction reaction. Though processes 400-13, 400-14, and 400-15 are illustrated as involving the reducing agents $LiAlH_4$ and $H_2$ with Pd/C, in some embodiments, other reducing agents are used (e.g., sodium borohydride ($NaBH_4$), carbon monoxide (CO), iron(II) compounds, etc.).

In process 400-13, the PG-phenol-substituted aconitic acid derivative 448 is reacted with hydrogen ($H_2$) in an ethanol solution. The reaction is catalyzed by palladium on carbon (Pd/C), and produces the PG-phenol-substituted carboxysuccinic acid derivative 452. In process 400-14, the PG-phenol-substituted aconitic acid derivative 448 is reacted with lithium aluminum hydride ($LiAlH_4$) in an ether solution, producing the PG-phenol-substituted butenetriol derivative 456. In process 400-15, the PG-phenol-substituted butenetriol derivative 456 is reacted with hydrogen ($H_2$) in an ethanol (EtOH) solution. The reaction is catalyzed by a palladium on carbon (Pd/C) catalyst, and produces the PG-phenol-substituted butanetriol derivative 460.

Figure 4G:
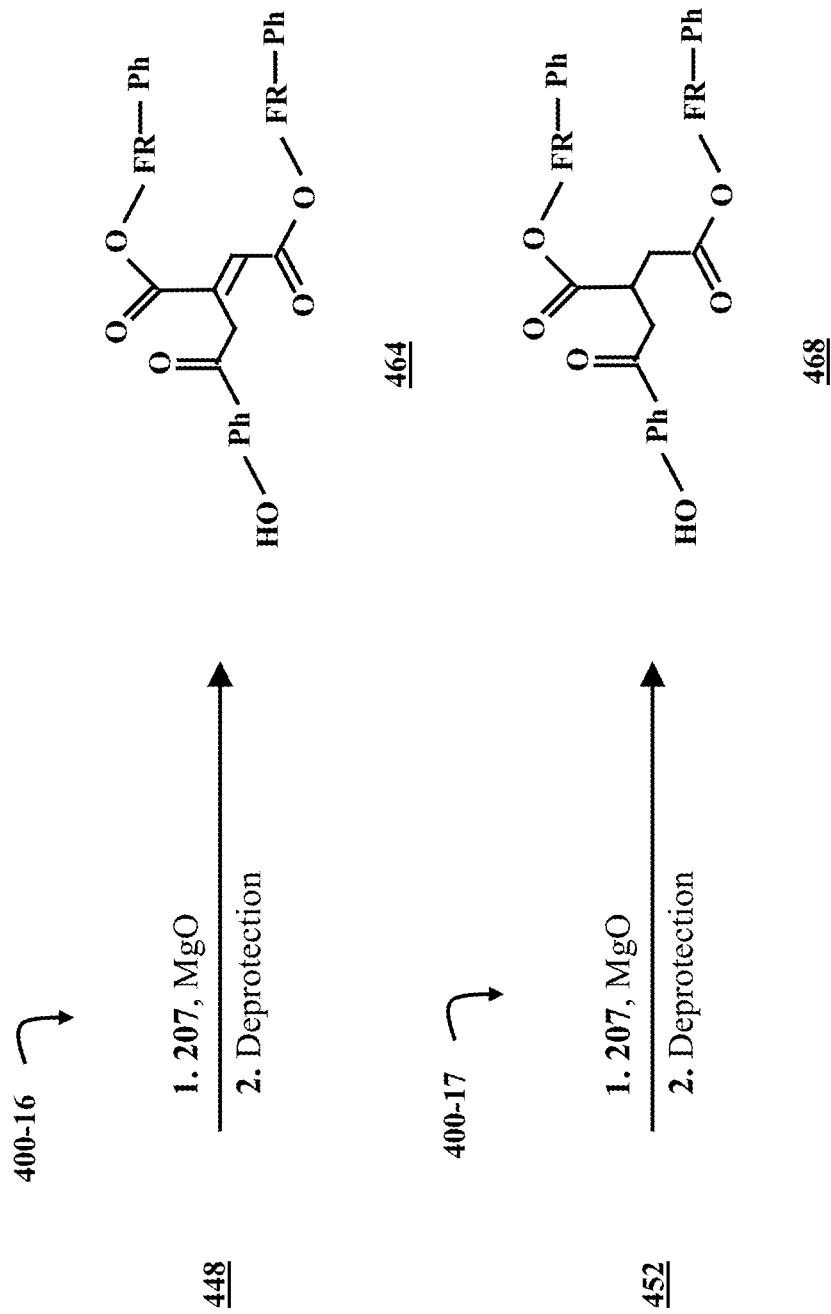
FIG. 4G is a chemical reaction diagram illustrating processes of forming phenol-functionalized aconitic acid and carboxysuccinic acid derivatives, according to some embodiments of the present disclosure.

FIG. 4G is a chemical reaction diagram illustrating processes 400-16 and 400-17 of forming a phenol-functionalized aconitic acid derivative 464 and a carboxysuccinic acid derivative 468, according to some embodiments of the present disclosure. Each process involves a reaction with a phenyl-substituted phosphorus-based flame-retardant molecule 207, followed by a deprotection reaction. In process 400-16, the PG-phenol-substituted aconitic acid derivative 448 is converted to the phenol-functionalized aconitic acid derivative 464. In process 400-17, the PG-phenol-substituted carboxysuccinic acid derivative 452 is converted to the phenol-functionalized carboxysuccinic acid derivative 468. Processes 400-16 and 400-17 are carried out under substantially the same reaction conditions.

In the first step of processes 400-16 and 400-17, the PG-phenol-substituted aconitic acid derivative 448 is reacted with the phenyl-substituted phosphorus-based flame-retardant molecule 207 in the presence of magnesium oxide (MgO). This reaction binds phenyl-substituted flame-retardant (Ph-FR) moieties to the hydroxyl groups on the PG-phenol-substituted derivatives 448 or 452. If processes 400-16 and 400-17 are carried out with the phenyl-substituted phosphate-based flame-retardant molecule 207-1, the phenol-functionalized derivatives 464 and 468 will have phosphoryl Ph-FR groups, and, if the processes 400-16 and 400-17 are carried out with the phosphonate-based flame-retardant molecule 207-2, the phenol-functionalized derivatives 464 and 468 will have phosphonyl Ph-FR groups. Additionally, in some embodiments, processes 400-16 and 400-17 are carried out with a mixture of phenyl-substituted phosphorus-based flame-retardant molecules 207-1 and 207-2.

The second step in processes 400-16 and 400-17 is a deprotection reaction. In this step, the protecting group (PG) is removed. The reaction conditions under which the PG is removed can vary. For example, silyl PGs (e.g., TMS, TES, TBS, and TIPS) can be removed by a reaction with fluorides, such as tetrabutylammonium fluoride (TMF). The silyl PGs, as well as other PGs (e.g., MOM and THP) can also be removed by acids and bases. The deprotection reactions yield the phenol-functionalized aconitic acid derivative 464 and the phenol-functionalized carboxysuccinic acid derivative 468.

Figure 4H:
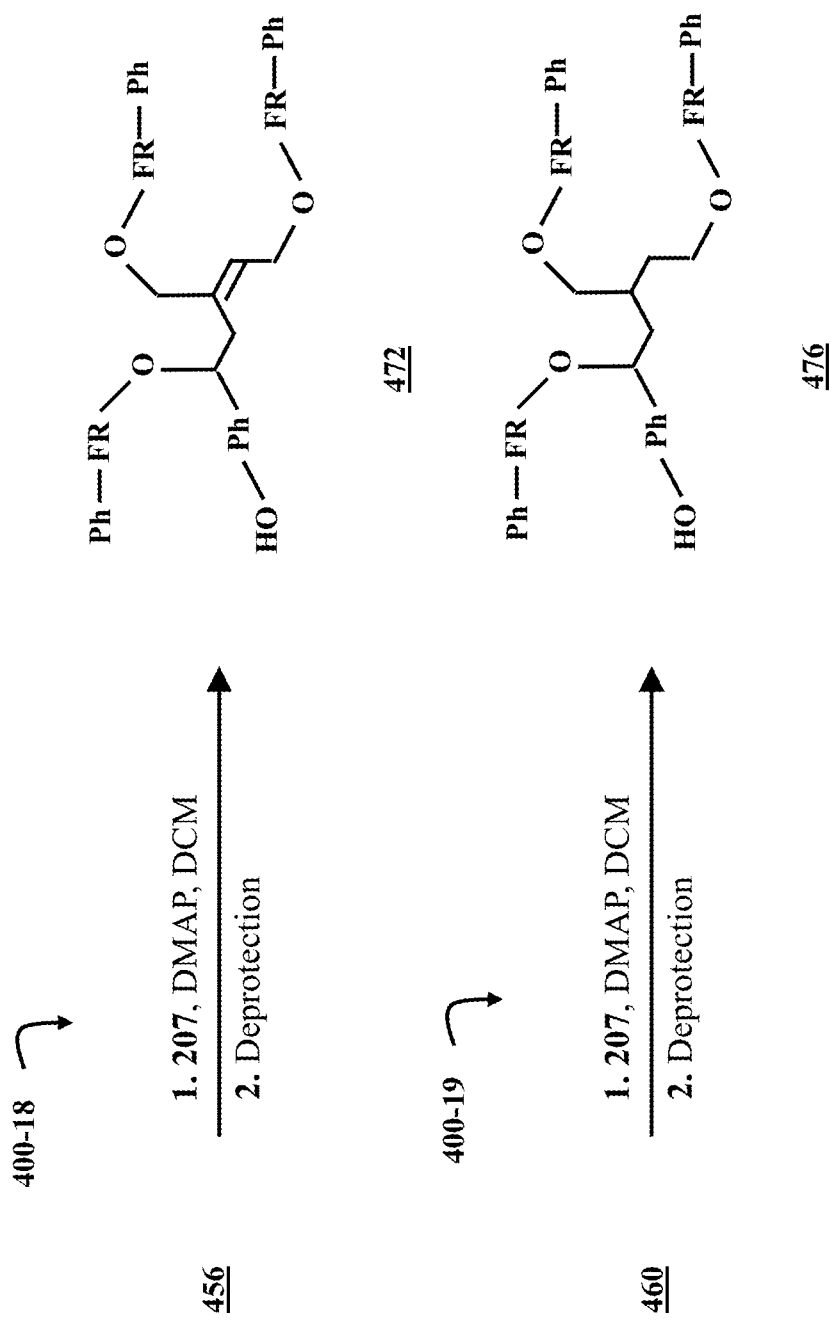
FIG. 4H is a chemical reaction diagram illustrating processes of forming phenol-functionalized butenetriol and butanetriol derivatives, according to some embodiments of the present disclosure.

FIG. 4H is a chemical reaction diagram illustrating processes 400-18 and 400-19 of forming a phenol-functionalized butenetriol derivative 472 and a phenol-functionalized butanetriol derivative 476, according to some embodiments of the present disclosure. Each process involves a reaction with a phenyl-substituted phosphorus-based flame-retardant molecule 207, followed by a deprotection reaction. In process 400-17, the PG-phenol-substituted butenetriol derivative 456 is converted to the phenol-functionalized flame-retardant butenetriol derivative 472. In process 400-19, the PG-phenol-substituted butanetriol derivative 460 is converted to the phenol-functionalized butanetriol derivative 476. Processes 400-18 and 400-19 are carried out under substantially the same reaction conditions as processes 400-16 and 400-17, respectively. Processes 400-16 and 400-17 are discussed in greater detail with regard to FIG. 4G.

In some embodiments, processes 400-16-400-19 are carried out with a mixture of phenyl-substituted phosphate- and phosphonate-based flame-retardant molecules 207-1 and 207-2. Carrying out processes 400-16-400-19 with a mixture of 207-1 and 207-2 can result in substituted flame-retardant molecules with both phosphoryl- and phosphonyl FR groups. However, in some instances, adding a mixture of both phenyl-substituted phosphorus-based flame-retardant molecules 207-1 and 207-2 can result in the production of phenol-functionalized flame-retardant molecules with all phosphoryl or all phosphonyl FR groups. Additionally, adding both phenyl-substituted phosphorus-based flame-retardant molecules 207-1 and 207-2 to the reaction can yield a mixture of products that includes some combination of derivatives with either all phosphoryl or all phosphonyl FR groups and derivatives with both phosphoryl and phosphonyl FR groups.

Figure 5A:
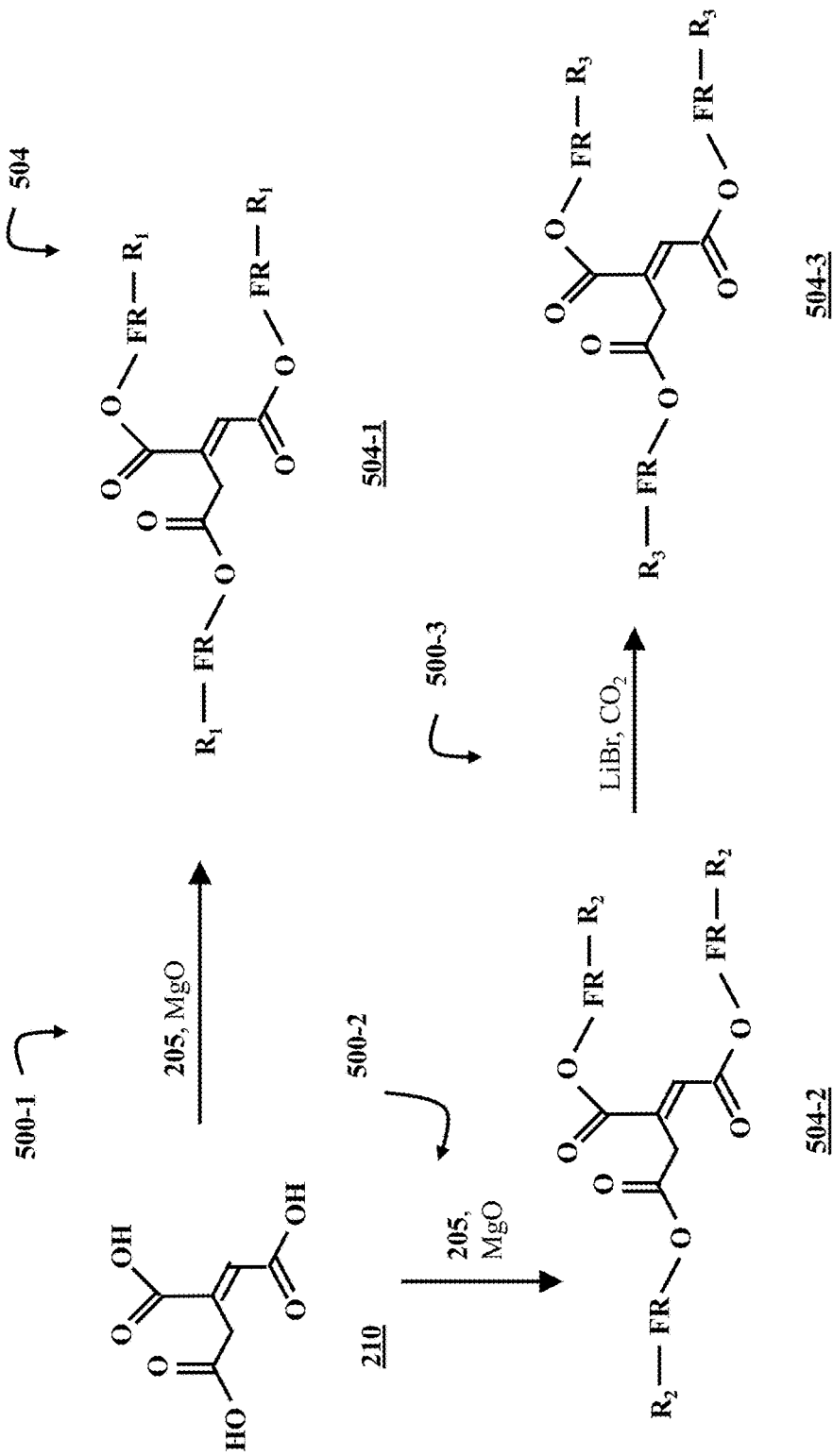
FIG. 5A is a chemical reaction diagram illustrating processes of synthesizing tri-functionalized flame-retardant aconitic acid-derived monomers, according to some embodiments of the present disclosure.

FIG. 5A is a chemical reaction diagram illustrating processes 500-1, 500-2, and 500-3 of synthesizing tri-functionalized flame-retardant aconitic acid-derived monomers 504, according to some embodiments of the present disclosure. In process 500-1, aconitic acid 210 is reacted with the phosphorus-based molecule 205 having allyl R groups 215-1. Magnesium oxide (MgO) is added to the reaction mixture, producing a tri-allyl-functionalized flame-retardant aconitic acid-derived monomer 504-1. Process 500-2 produces a tri-epoxy-functionalized flame-retardant aconitic acid derived monomer 504-2, and is carried out under substantially the same conditions as process 500-1, except that aconitic acid 210 is reacted with the phosphorus-based molecule 205 having epoxy R groups 215-2. In process 500-3, the tri-epoxy-functionalized flame-retardant aconitic acid derived monomer 504-2 is combined with lithium bromide (LiBr). Carbon dioxide ($CO_2$) is added to the mixture, yielding a tri-propylene carbonate-functionalized flame-retardant aconitic acid-derived monomer 504-3.

Figure 5B:
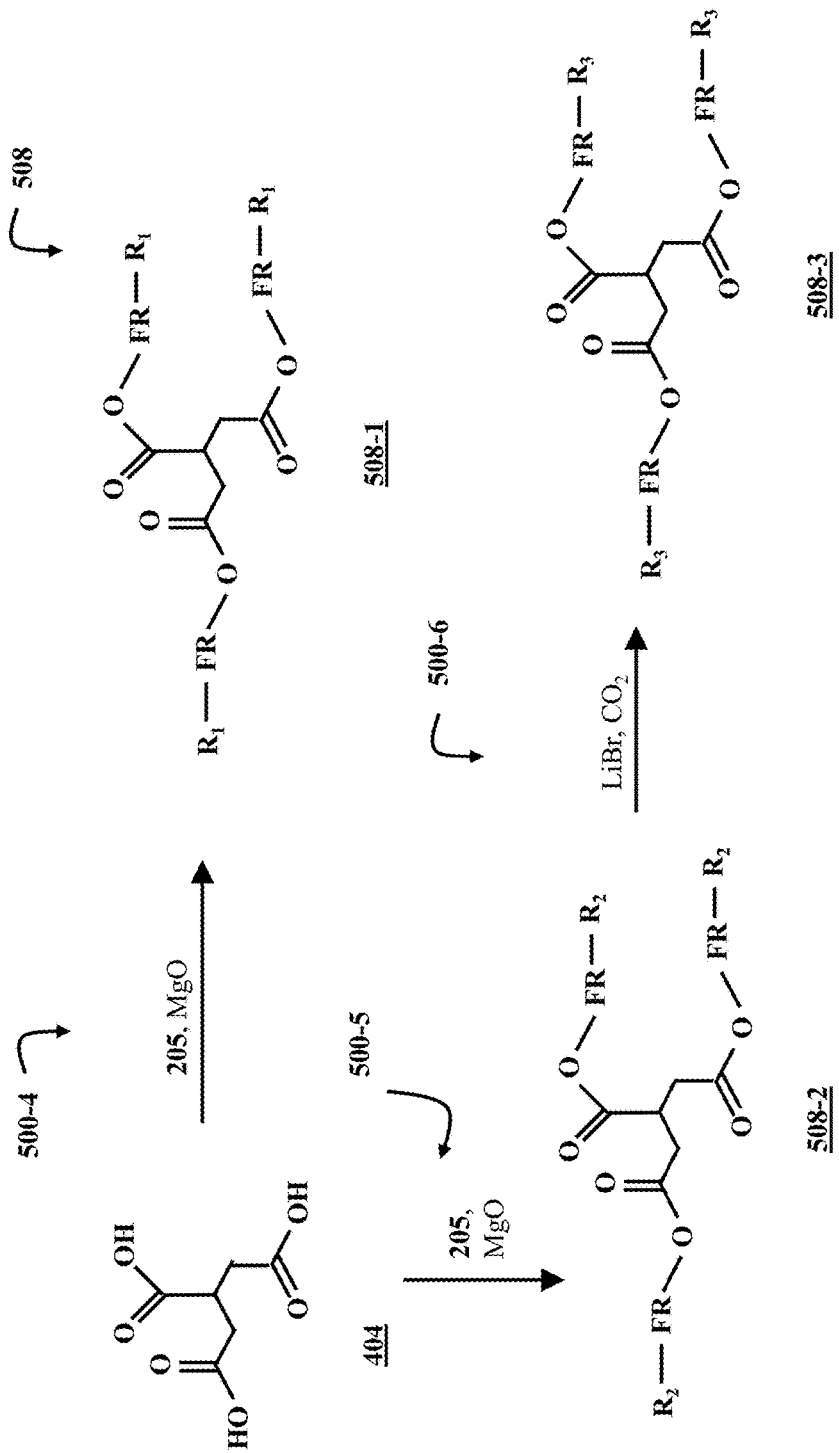
FIG. 5B is a chemical reaction diagram illustrating processes of synthesizing tri-functionalized flame-retardant carboxysuccinic acid-derived monomers, according to some embodiments of the present disclosure.

FIG. 5B is a chemical reaction diagram illustrating processes 500-4, 500-5, and 500-6 of synthesizing tri-functionalized flame-retardant carboxysuccinic acid-derived monomers 508, according to some embodiments of the present disclosure. In process 500-4, carboxysuccinic acid 404 is reacted with the phosphorus-based molecule 205 having allyl R groups 215-1. Magnesium oxide (MgO) is added to the reaction mixture, producing a tri-allyl-functionalized flame-retardant carboxysuccinic acid-derived monomer 508-1. Process 500-5 produces a tri-epoxy-functionalized flame-retardant carboxysuccinic acid-derived monomer 508-2, and is carried out under substantially the same conditions as process 500-4, except that carboxysuccinic acid 404 is reacted with the phosphorus-based molecule 205 having epoxy R groups 215-2. In process 500-6, the tri-epoxy-functionalized flame-retardant carboxysuccinic acid derived monomer 508-2 is combined with lithium bromide (LiBr). Carbon dioxide ($CO_2$) is added to the mixture, yielding a tri-propylene carbonate-functionalized flame-retardant carboxysuccinic acid-derived monomer 508-3.

Figure 5C:
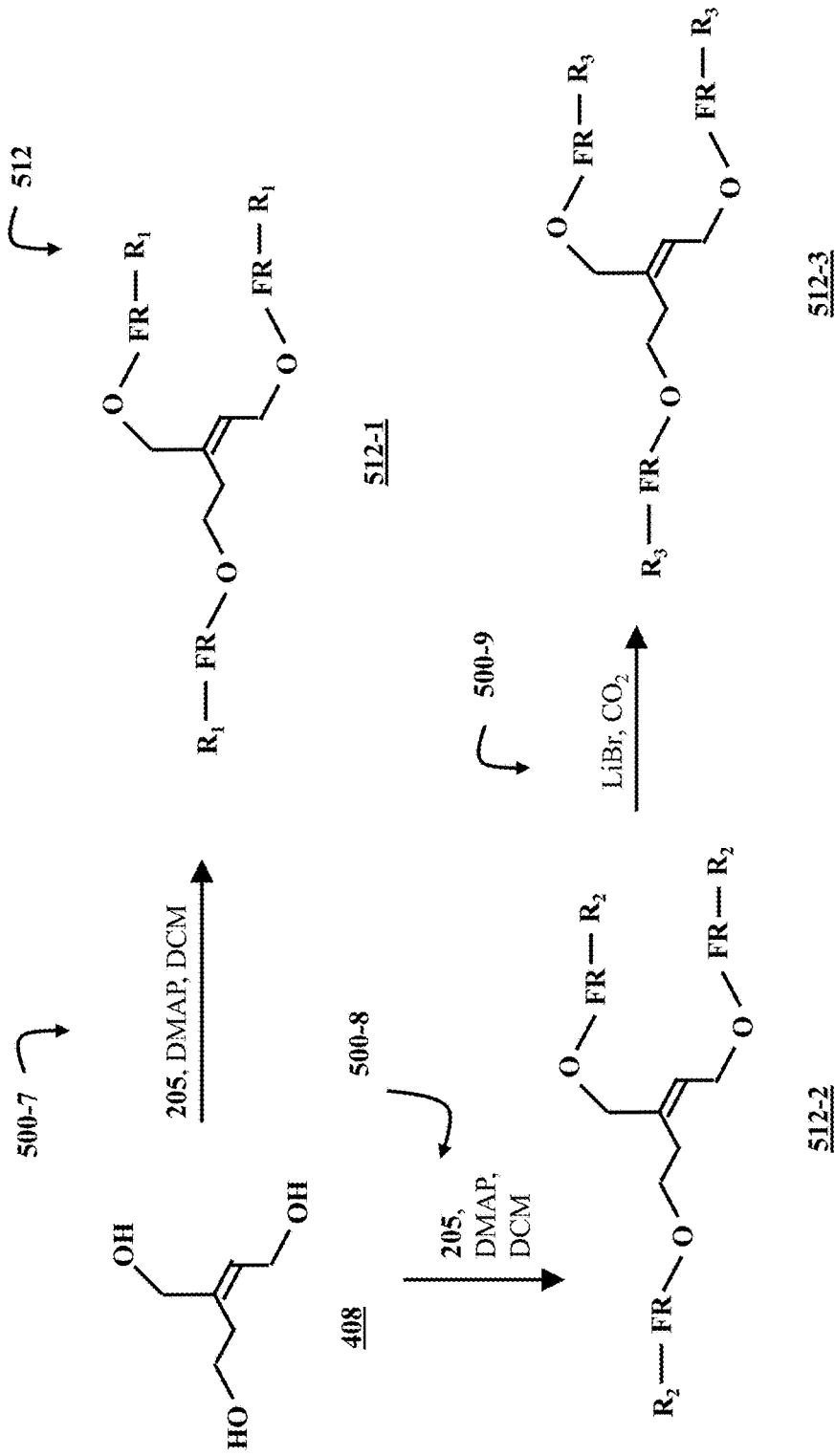
FIG. 5C is a chemical reaction diagram illustrating processes of synthesizing tri-functionalized flame-retardant butenetriol-derived monomers, according to some embodiments of the present disclosure.

FIG. 5C is a chemical reaction diagram illustrating processes 500-7, 500-8, and 500-9 of synthesizing tri-functionalized flame-retardant butenetriol-derived monomers 512, according to some embodiments of the present disclosure. In process 500-7, the butenetriol 408 is reacted with the phosphorus-based molecule 205 having allyl R groups 215-1. Dimethylaminopyridine (DMAP) in dichloromethane (DCM) is added to the reaction mixture, producing a tri-allyl-functionalized flame-retardant butenetriol-derived monomer 512-1. Process 500-8 produces a tri-epoxy-functionalized flame-retardant butenetriol-derived monomer 512-2, and is carried out under substantially the same conditions as process 500-7, except that the butenetriol 408 is reacted with the phosphorus-based molecule 205 having epoxy R groups 215-2. In process 500-9, the tri-epoxy-functionalized flame-retardant butenetriol-derived monomer 512-2 is combined with lithium bromide (LiBr). Carbon dioxide ($CO_2$) is added to the mixture, yielding a tri-propylene carbonate-functionalized flame-retardant butenetriol-derived monomer 512-3.

Figure 5D:
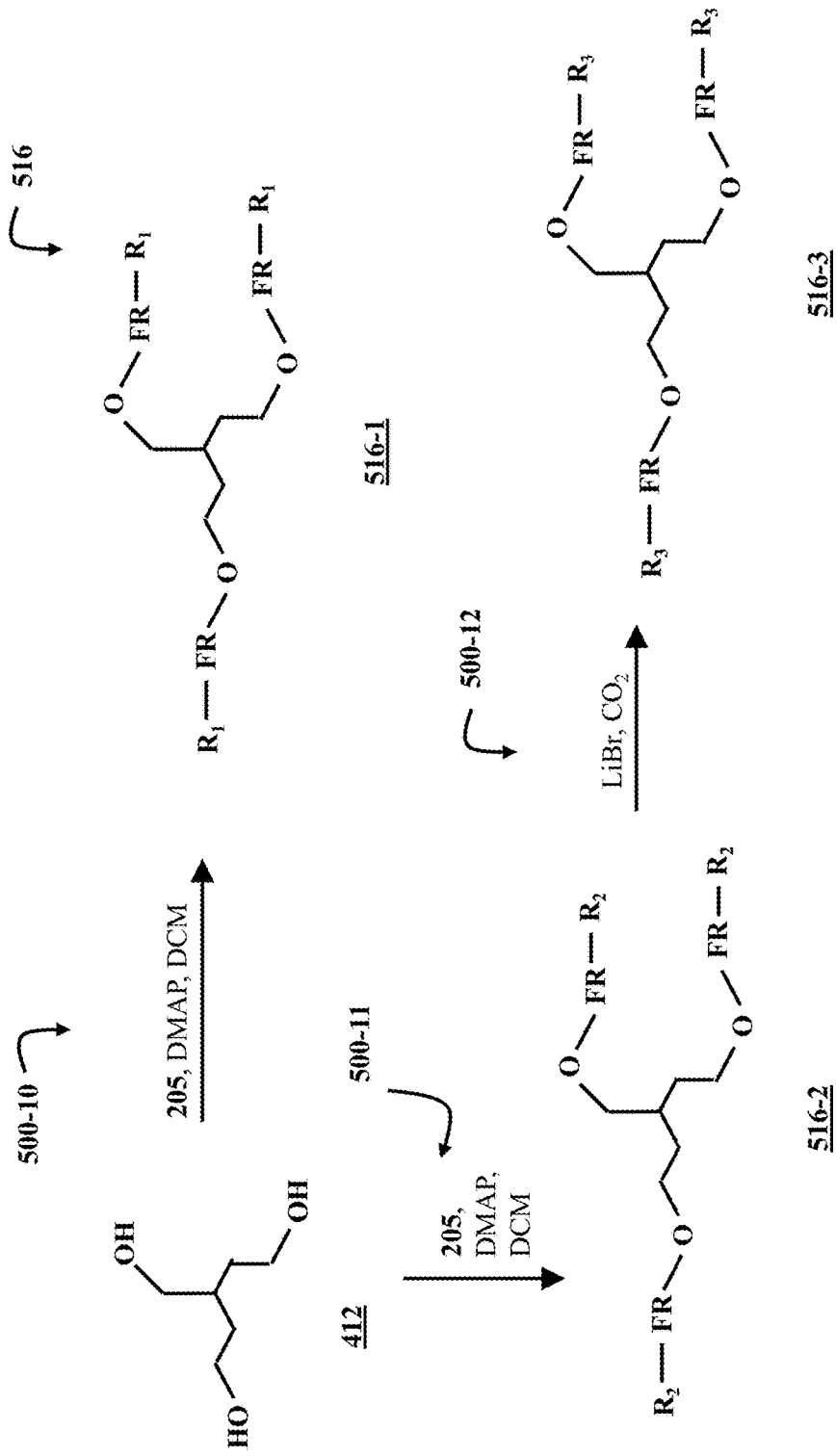
FIG. 5D is a chemical reaction diagram illustrating processes of synthesizing tri-functionalized flame-retardant butanetriol-derived monomers, according to some embodiments of the present disclosure.
Figure 5E:
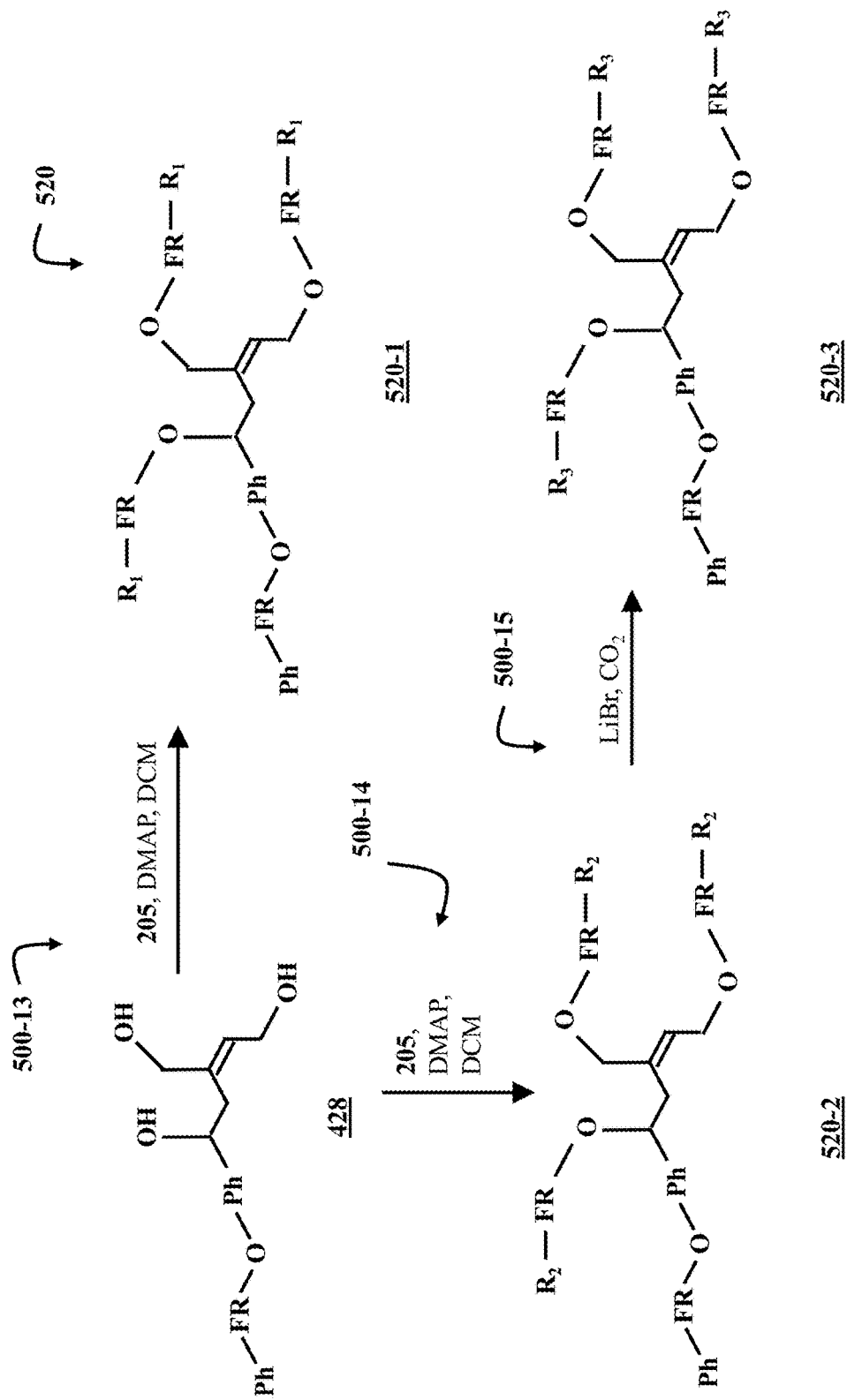
FIG. 5E is a chemical reaction diagram illustrating processes of synthesizing tri-functionalized mono-Ph-FR flame-retardant butenetriol-derived monomers, according to some embodiments of the present disclosure.
Figure 5F:
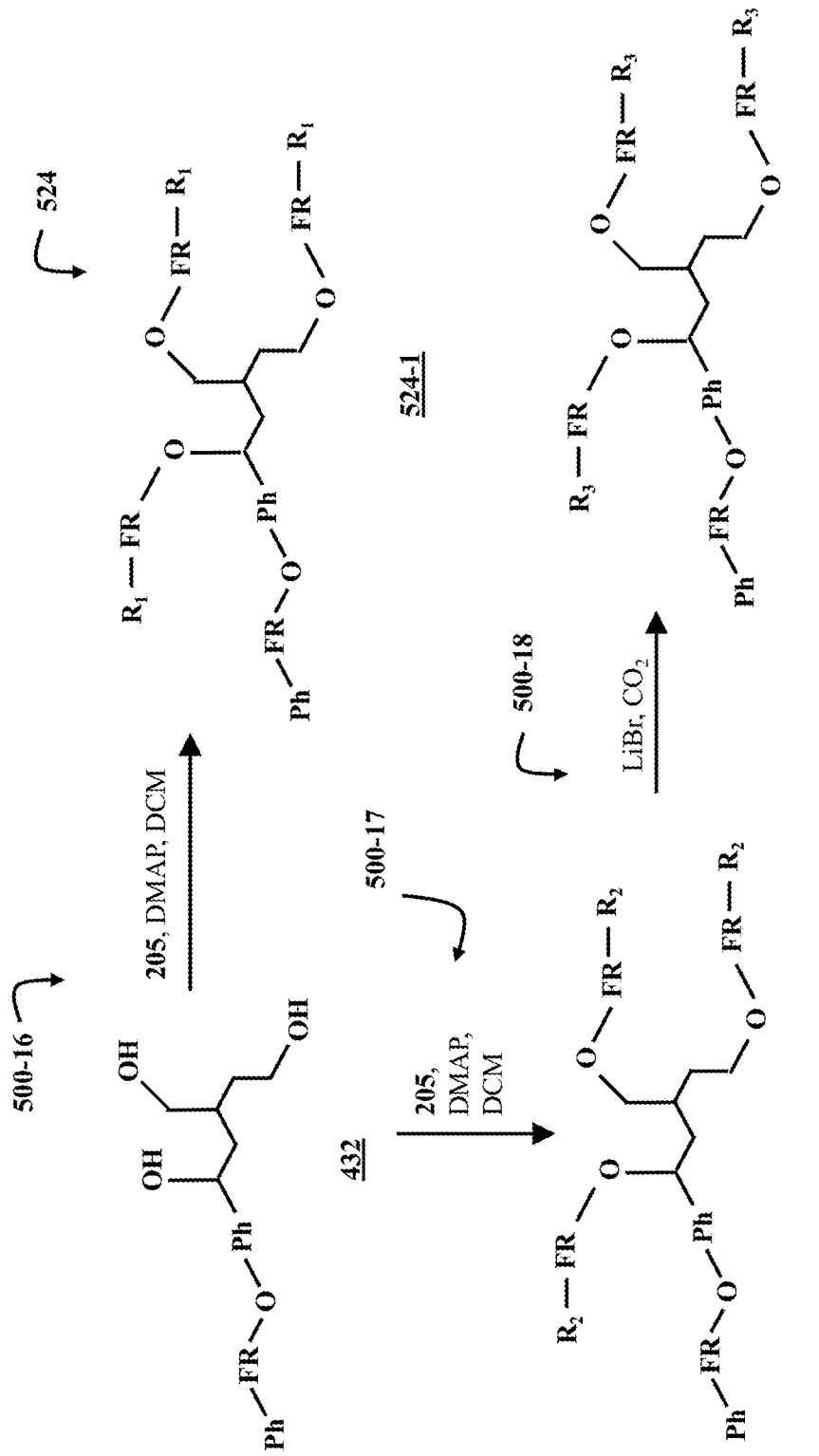
FIG. 5F is a chemical reaction diagram illustrating processes synthesizing tri-functionalized mono-Ph-FR flame-retardant butanetriol-derived monomers, according to some embodiments of the present disclosure.

FIG. 5D is a chemical reaction diagram illustrating processes 500-10, 500-11, and 500-12 of synthesizing tri-functionalized flame-retardant butanetriol-derived monomers 516, according to some embodiments of the present disclosure. In process 500-10, the butanetriol 412 is reacted with the phosphorus-based molecule 205 having allyl R groups 215-1. Dimethylaminopyridine (DMAP) in dichloromethane (DCM) is added to the reaction mixture, producing a tri-allyl-functionalized flame-retardant butanetriol-derived monomer 516-1. Process 500-11 produces a tri-epoxy-functionalized flame-retardant butanetriol-derived monomer 516-2, and is carried out under substantially the same conditions as process 500-10, except that the butanetriol 412 is reacted with the phosphorus-based molecule 205 having epoxy R groups 215-2. In process 500-12, the tri-epoxy-functionalized flame-retardant butanetriol-derived monomer 516-2 is combined with lithium bromide (LiBr). Carbon dioxide ($CO_2$) is added to the mixture, yielding a tri-propylene carbonate-functionalized flame-retardant butanetriol-derived monomer 516-3.

FIG. 5E is a chemical reaction diagram illustrating processes 500-13, 500-14, and 500-15 of synthesizing tri-functionalized mono-Ph-FR flame-retardant butenetriol-derived monomers 520, according to some embodiments of the present disclosure. Each monomer 520 has a single phenyl (Ph)-substituted FR group in addition to its R-functionalized FR groups. In process 500-13, the mono-Ph-FR butenetriol derivative 428 is reacted with the phosphorus-based molecule 205 having allyl R groups 215-1. Dimethylaminopyridine (DMAP) in dichloromethane (DCM) is added to the reaction mixture, producing a tri-allyl-functionalized mono-Ph-FR flame-retardant butenetriol-derived monomer 520-1.

Process 500-14 produces a tri-epoxy-functionalized mono-Ph-FR flame-retardant butenetriol-derived monomer 520-2, and is carried out under substantially the same conditions as process 500-13, except that the mono-Ph-FR butenetriol derivative 428 is reacted with the phosphorus-based molecule 205 having epoxy R groups 215-2. In process 500-15, the tri-epoxy-functionalized mono-Ph-FR flame-retardant butenetriol-derived monomer 520-2 is combined with lithium bromide (LiBr). Carbon dioxide ($CO_2$) is added to the mixture, yielding a tri-propylene carbonate-functionalized mono-Ph-FR flame-retardant butenetriol-derived monomer 520-3.

FIG. 5F is a chemical reaction diagram illustrating processes 500-16, 500-17, and 500-18 of synthesizing tri-functionalized mono-Ph-FR flame-retardant butanetriol-derived monomers 524, according to some embodiments of the present disclosure. Each monomer 524 has a single phenyl (Ph)-substituted FR (phosphoryl or phosphonyl) moiety. In process 500-16, the mono-Ph-FR butanetriol derivative 432 is reacted with an R-functionalized phosphorus-based molecule 205 having allyl R groups 215-1. Dimethylaminopyridine (DMAP) in dichloromethane (DCM) is added to the reaction mixture, producing a tri-allyl-functionalized mono-Ph-FR flame-retardant butanetriol-derived monomer 524-1.

Process 500-17 produces a tri-epoxy-functionalized mono-Ph-FR flame-retardant butanetriol-derived monomer 524-2, and is carried out under substantially the same conditions as process 500-16, except that the mono-Ph-FR butanetriol derivative 432 is reacted with an R-functionalized phosphorus-based molecule 205 having epoxy R groups 215-2. In process 500-15, the tri-epoxy-functionalized mono-Ph-FR flame-retardant butanetriol-derived monomer 524-2 is combined with lithium bromide (LiBr). Carbon dioxide ($CO_2$) is added to the mixture, yielding a tri-propylene carbonate-functionalized mono-Ph-FR flame-retardant butanetriol-derived monomer 524-3.

Figure 6A:
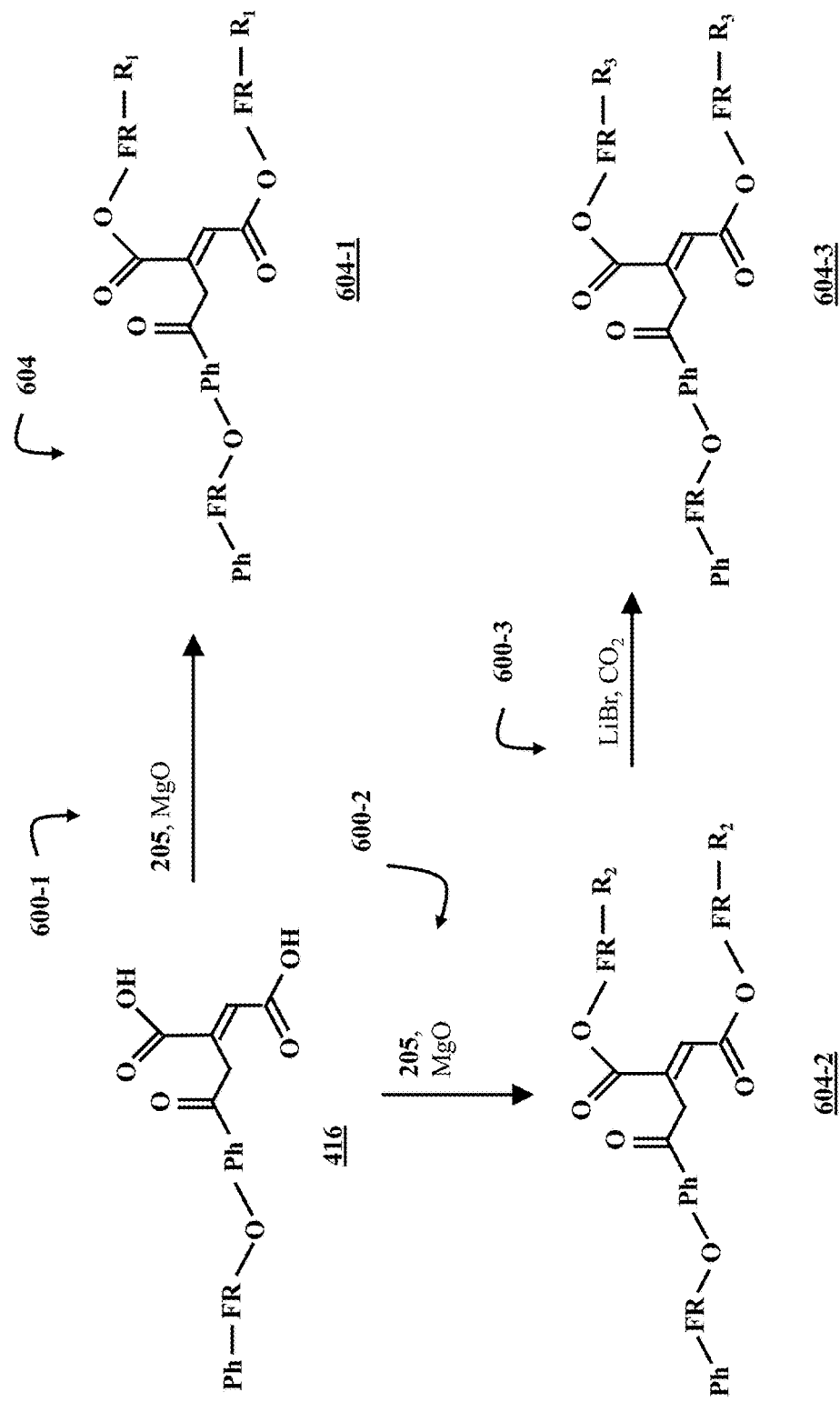
FIG. 6A is a chemical reaction diagram illustrating processes of forming di-functionalized mono-Ph-FR flame-retardant aconitic acid-derived monomers, according to some embodiments of the present disclosure.
Figure 6B:
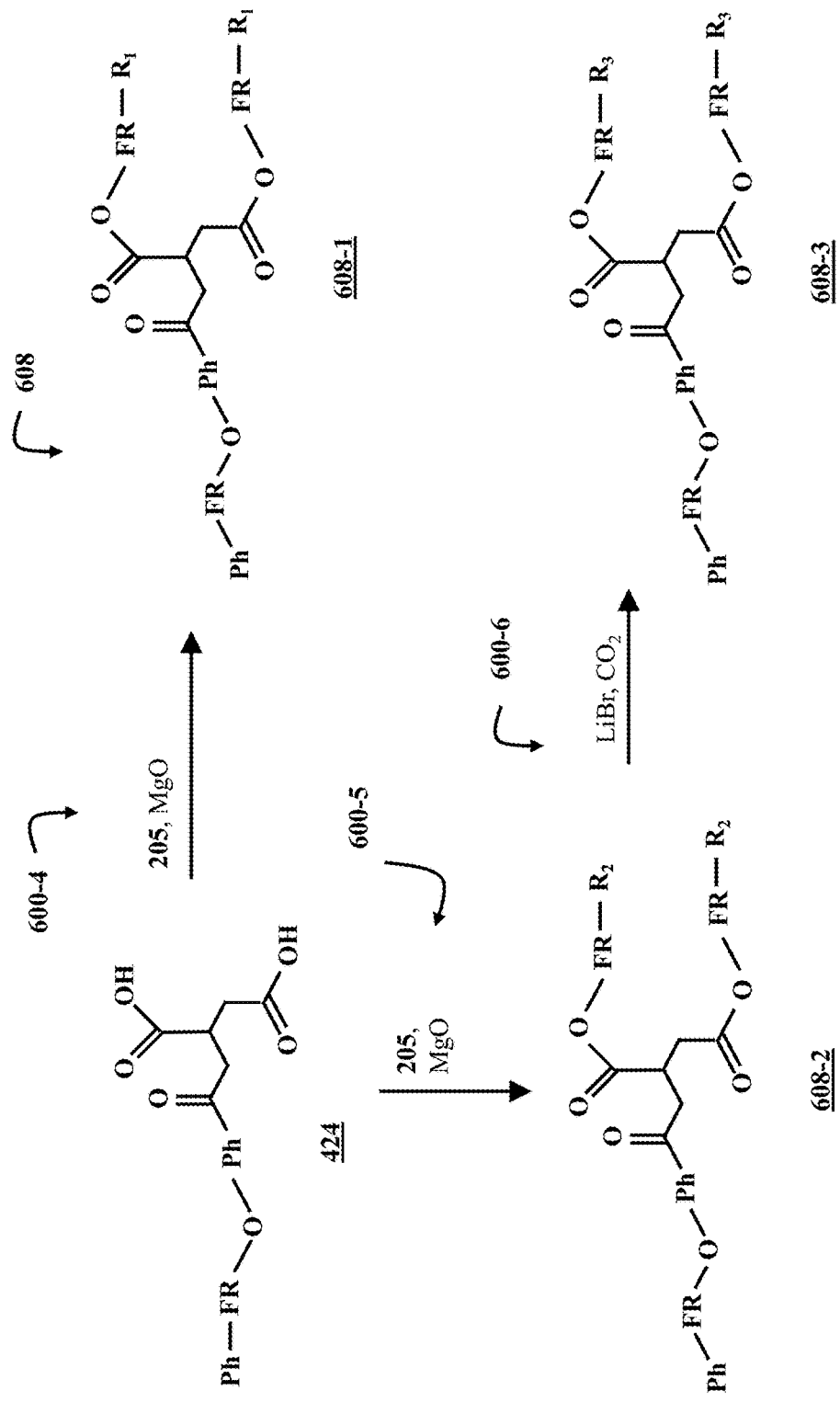
FIG. 6B is a chemical reaction diagram illustrating processes of forming di-functionalized mono-Ph-FR flame-retardant carboxysuccinic acid-derived monomers, according to some embodiments of the present disclosure.

FIG. 6A is a chemical reaction diagram illustrating processes 600-1, 600-2, and 600-3 of forming di-functionalized mono-Ph-FR flame-retardant aconitic acid-derived monomers 604, according to some embodiments of the present disclosure. Each monomer 604 has a single phenyl (Ph)-substituted FR group. In processes 600-1 and 500-2, the mono-Ph-FR aconitic acid derivative 416 is converted to a di-allyl-functionalized mono-Ph-FR flame-retardant aconitic acid-derived monomer 604-1 and a di-epoxy-functionalized mono-Ph-FR flame-retardant aconitic acid-derived monomer 604-2, respectively. In process 600-3, the di-epoxy functionalized mono-Ph-FR flame-retardant aconitic acid-derived monomer 604-2 is converted to a di-propylene carbonate-functionalized mono-Ph-FR flame-retardant aconitic acid-derived monomer 604-3. Processes 600-1, 600-2, and 600-3 are carried out under substantially the same conditions as processes 500-1, 500-2, and 500-3, respectively. Processes 500-1, 500-2, and 500-3 are discussed in greater detail with regard to FIG. 5A.

FIG. 6B is a chemical reaction diagram illustrating processes 600-4, 600-5, and 600-6 of forming di-functionalized mono-Ph-FR flame-retardant carboxysuccinic acid-derived monomers 608, according to some embodiments of the present disclosure. Each monomer 608 has a single phenyl (Ph)-substituted FR group. In processes 600-4 and 500-5, the mono-Ph-FR carboxysuccinic acid derivative 424 is converted to a di-allyl functionalized mono-Ph-FR flame-retardant carboxysuccinic acid-derived monomer 608-1 and a di-epoxy-functionalized mono-Ph-FR flame-retardant carboxysuccinic acid-derived monomer 608-2, respectively. In process 600-5, the di-epoxy-functionalized mono-Ph-FR flame-retardant carboxysuccinic acid-derived monomer 608-2 is converted to a di-propylene carbonate-functionalized mono-Ph-FR flame-retardant carboxysuccinic acid-derived monomer 608-3. Processes 600-4, 600-5, and 600-6 are carried out under substantially the same conditions as processes 500-1, 500-2, and 500-3, respectively.

Figure 6C:
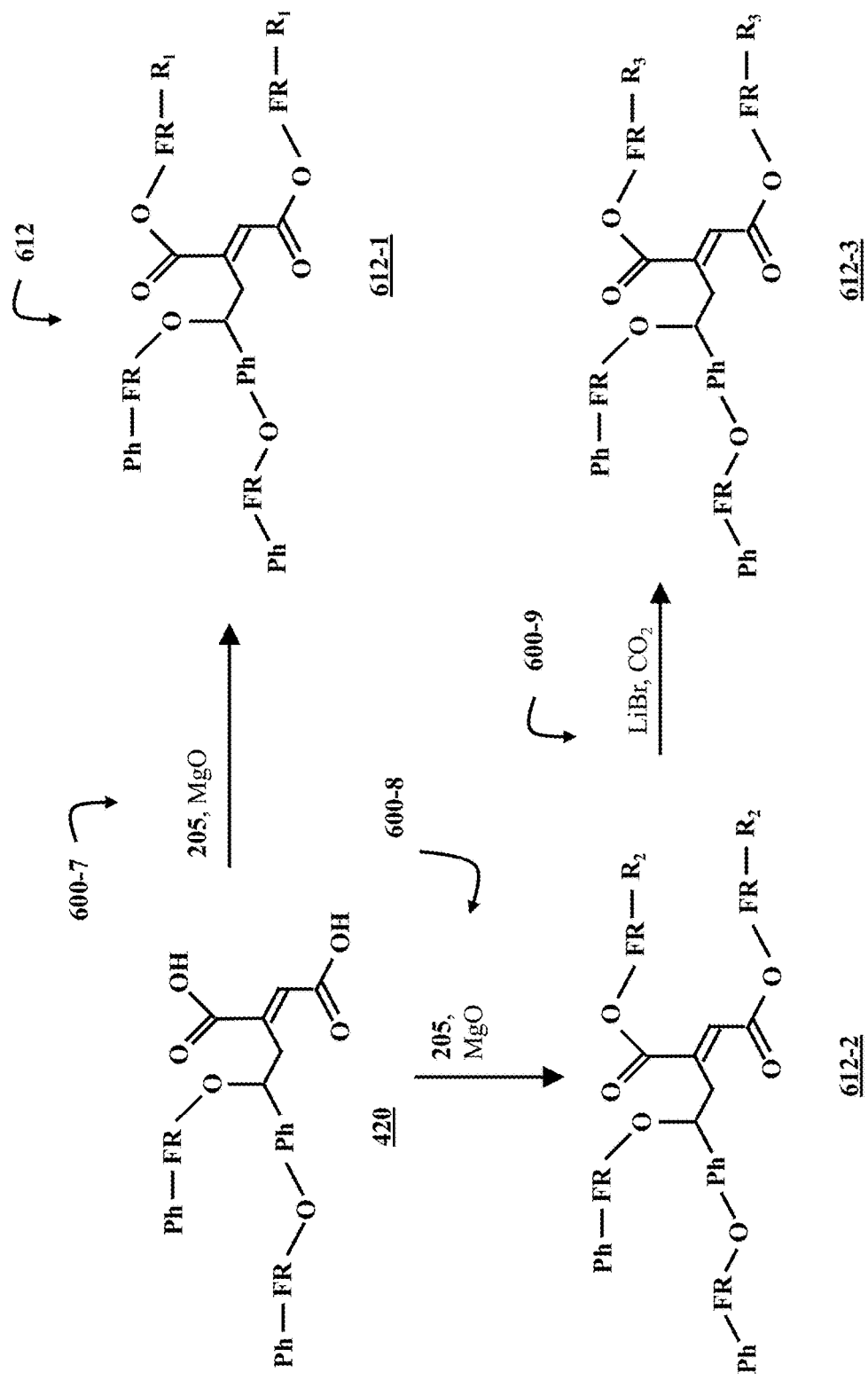
FIG. 6C is a chemical reaction diagram illustrating processes of forming di-functionalized di-Ph-FR flame-retardant aconitic acid-derived monomers, according to some embodiments of the present disclosure.
Figure 6D:
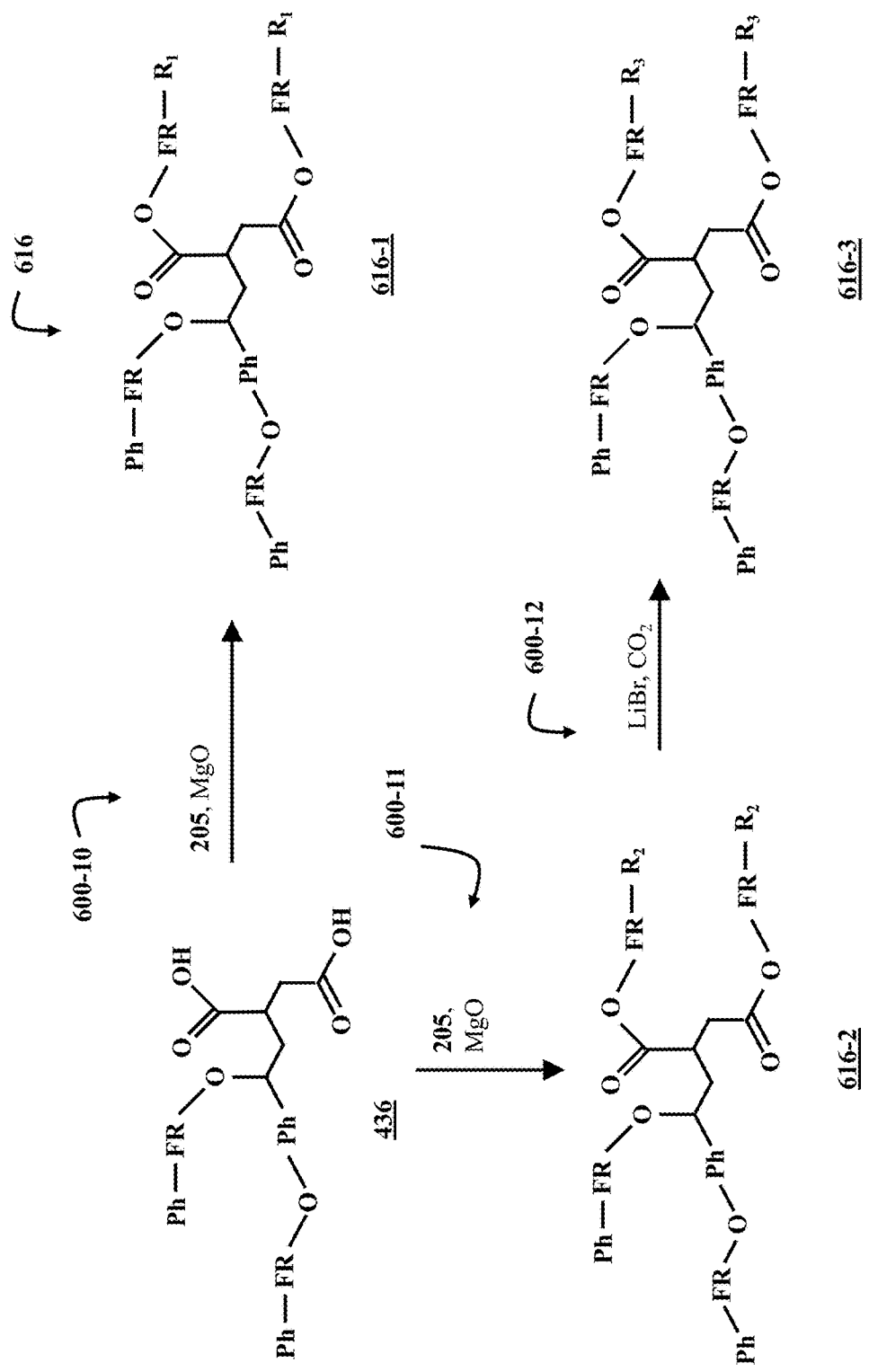
FIG. 6D is a chemical reaction diagram illustrating processes of forming di-functionalized di-Ph-FR flame-retardant carboxysuccinic acid-derived monomers, according to some embodiments of the present disclosure.
Figure 6E:
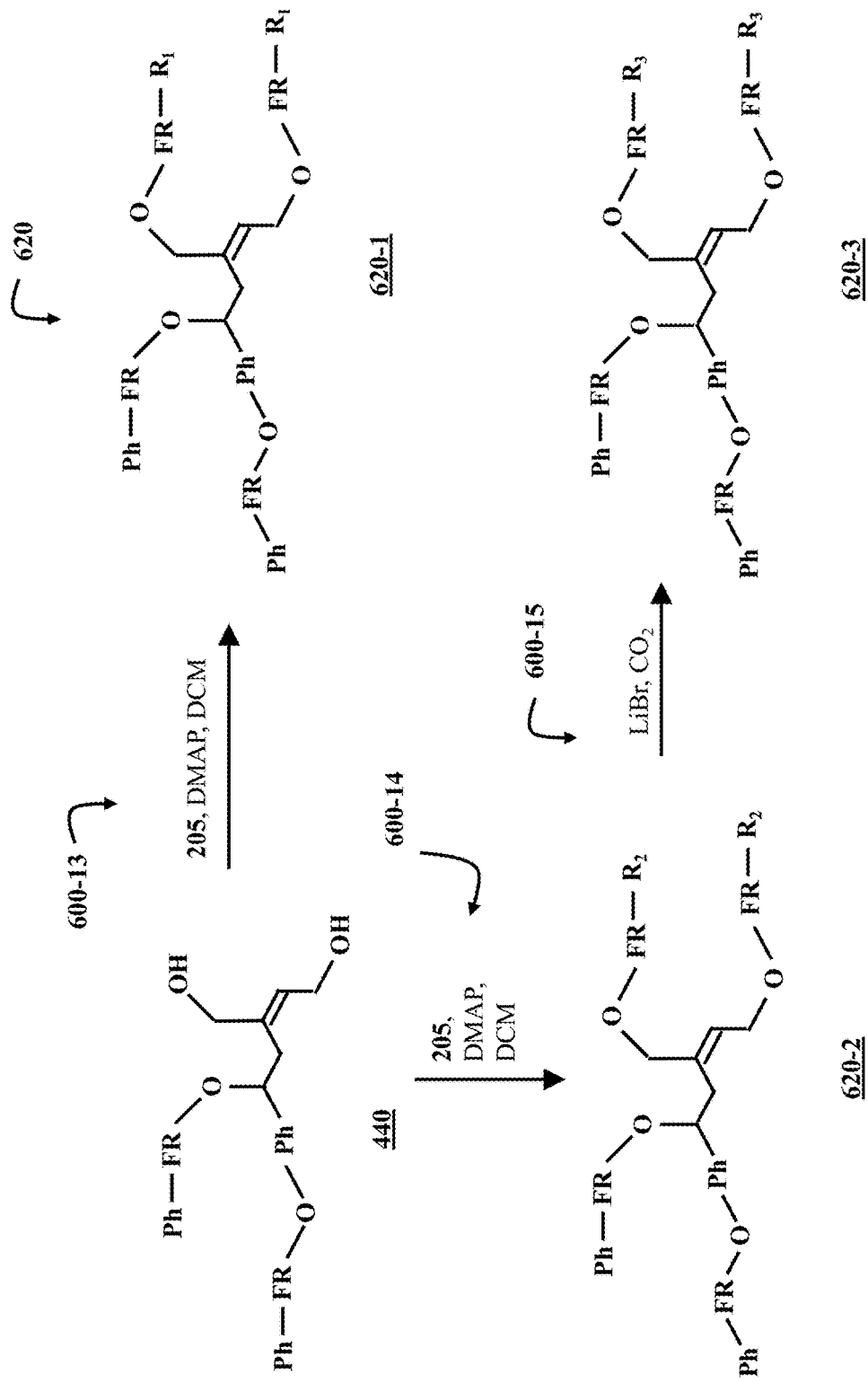
FIG. 6E is a chemical reaction diagram illustrating processes of forming di-functionalized di-Ph-FR flame-retardant butenetriol-derived monomers, according to some embodiments of the present disclosure.
Figure 6F:
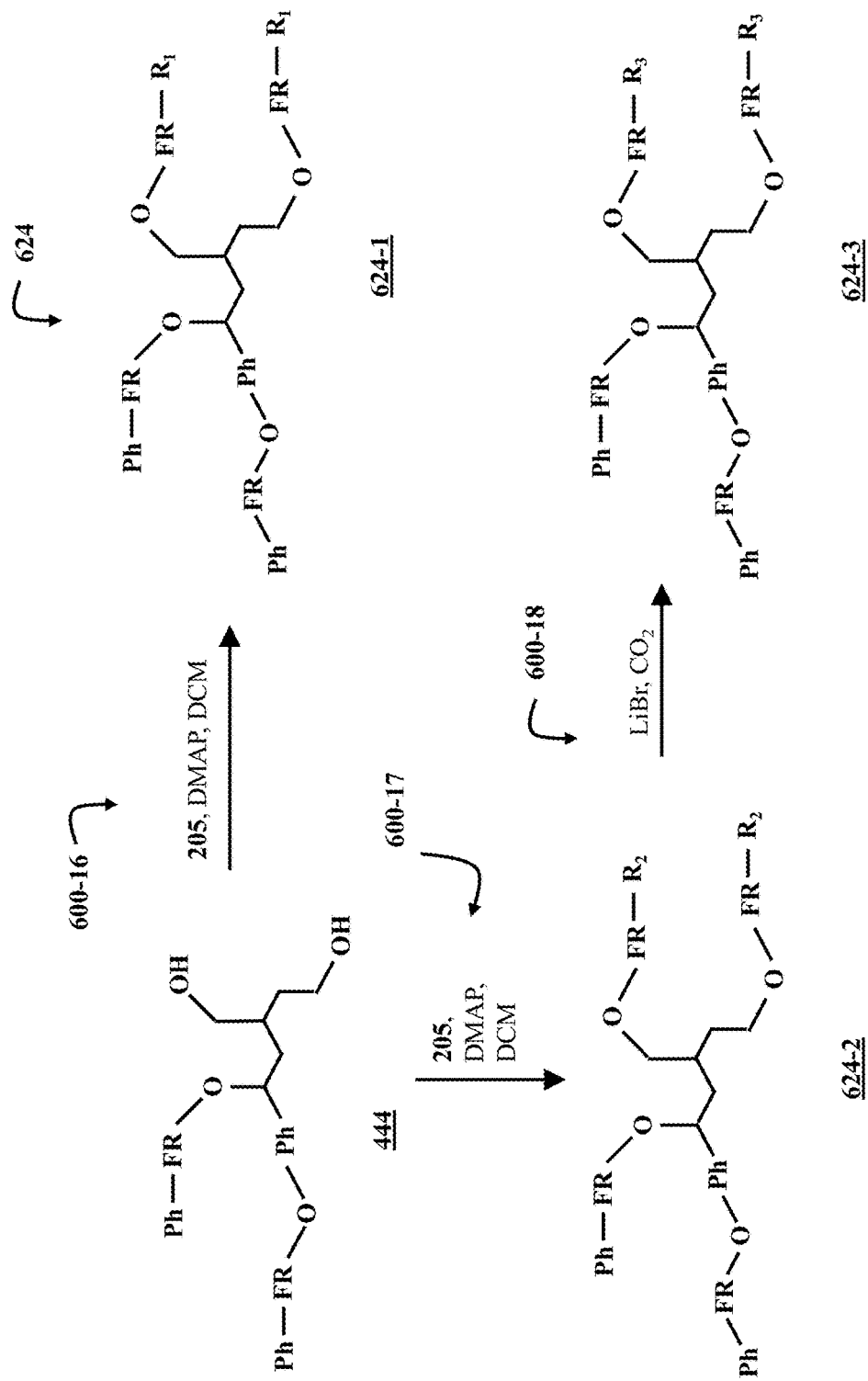
FIG. 6F is a chemical reaction diagram illustrating processes of forming di-functionalized di-Ph-FR flame-retardant butanetriol-derived monomers, according to some embodiments of the present disclosure.

FIG. 6C is a chemical reaction diagram illustrating processes 600-7, 600-8, and 600-9 of forming di-functionalized di-Ph-FR flame-retardant aconitic acid-derived monomers 612, according to some embodiments of the present disclosure. Each monomer 612 has two phenyl (Ph)-substituted FR groups, according to some embodiments of the present disclosure. In processes 600-7 and 500-8, the di-Ph-FR aconitic acid derivative 420 is converted to a di-allyl-functionalized di-Ph-FR flame-retardant aconitic acid-derived monomer 612-1 and a di-epoxy-functionalized di-Ph-FR flame-retardant aconitic acid-derived monomer 612-2, respectively. In process 600-9, the di-epoxy functionalized di-Ph-FR flame-retardant aconitic acid-derived monomer 612-2 is converted to a di-propylene carbonate-functionalized di-Ph-FR flame-retardant aconitic acid-derived monomer 612-3. Processes 600-7, 600-8, and 600-9 are carried out under substantially the same conditions as processes 500-1, 500-2, and 500-3, respectively.

FIG. 6D is a chemical reaction diagram illustrating processes 600-10, 600-11, and 600-12 of forming di-functionalized di-Ph-FR flame-retardant carboxysuccinic acid-derived monomers 616, according to some embodiments of the present disclosure. Each monomer 616 has two phenyl (Ph)-substituted FR groups. In processes 600-10 and 500-11, the di-Ph-FR carboxysuccinic acid derivative 436 is converted to a di-allyl functionalized di-Ph-FR flame-retardant carboxysuccinic acid-derived monomer 616-1 and a di-epoxy-functionalized di-Ph-FR flame-retardant carboxysuccinic acid-derived monomer 616-2, respectively. In process 600-12, the di-epoxy-functionalized di-Ph-FR flame-retardant carboxysuccinic acid-derived monomer 616-2 is converted to a di-propylene carbonate-functionalized di-Ph-FR flame-retardant carboxysuccinic acid-derived monomer 616-3. Processes 600-10, 600-11, and 600-12 are carried out under substantially the same conditions as processes 500-1, 500-2, and 500-3, respectively.

FIG. 6E is a chemical reaction diagram illustrating processes 600-13, 600-14, and 600-15 of forming di-functionalized di-Ph-FR flame-retardant butenetriol-derived monomers 620, according to some embodiments of the present disclosure. Each monomer 620 has two phenyl (Ph)-substituted FR groups. In processes 600-13 and 500-14, the di-Ph-FR butenetriol derivative 440 is converted to a di-allyl functionalized di-Ph-FR flame-retardant butenetriol-derived monomer 620-1 and a di-epoxy-functionalized di-Ph-FR flame-retardant butenetriol-derived monomer 620-2, respectively. In process 600-15, the di-epoxy-functionalized di-Ph-FR flame-retardant butenetriol-derived monomer 620-2 is converted to a di-propylene carbonate-functionalized di-Ph-FR flame-retardant butenetriol-derived monomer 620-3. Processes 600-13, 600-14, and 600-15 are carried out under substantially the same conditions as processes 500-13, 500-14, and 500-15, respectively. Processes 500-13, 500-14, and 500-15, are discussed in greater detail with regard to FIG. 5E.

FIG. 6F is a chemical reaction diagram illustrating processes 600-16, 600-17, and 600-18 of forming di-functionalized di-Ph-FR flame-retardant butanetriol-derived monomers 624, according to some embodiments of the present disclosure. Each monomer 624 has two phenyl (Ph)-substituted FR groups. In processes 600-16 and 500-17, the di-Ph-FR butanetriol derivative 444 is converted to a di-allyl functionalized di-Ph-FR flame-retardant butanetriol-derived monomer 624-1 and a di-epoxy-functionalized di-Ph-FR flame-retardant butanetriol-derived monomer 624-2, respectively. In process 600-18, the di-epoxy-functionalized di-Ph-FR flame-retardant butanetriol-derived monomer 624-2 is converted to a di-propylene carbonate-functionalized di-Ph-FR flame-retardant butanetriol-derived monomer 624-3. Processes 600-16, 600-17, and 600-18 are carried out under substantially the same conditions as processes 500-13, 500-14, and 500-15, respectively.

Figure 7A:
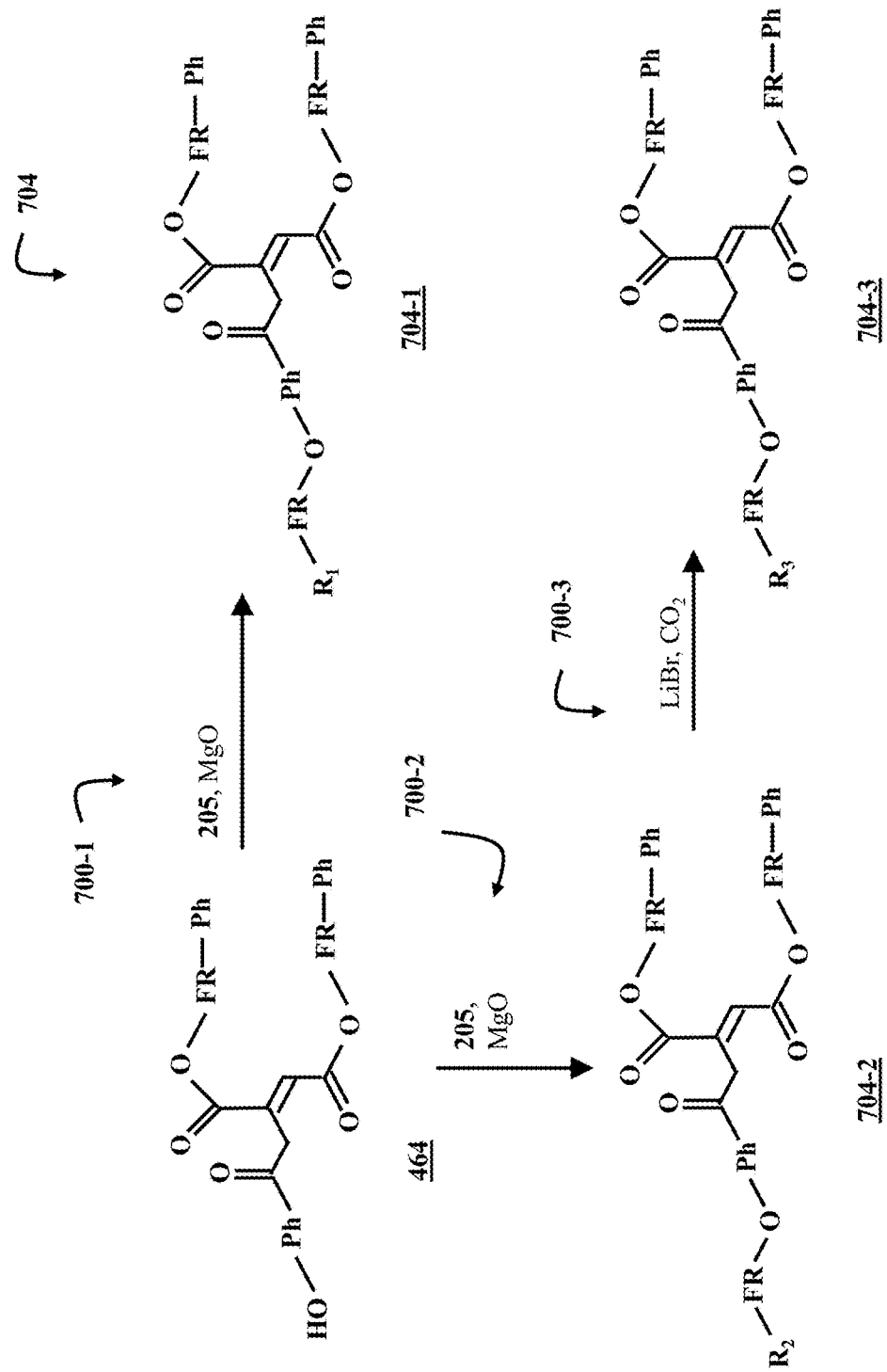
FIG. 7A is a chemical reaction diagram illustrating processes of forming mono-functionalized di-Ph-FR flame-retardant aconitic acid-derived monomers, according to some embodiments of the present disclosure.

FIG. 7A is a chemical reaction diagram illustrating processes 700-1, 700-2, and 700-3 of forming mono-functionalized di-Ph-FR flame-retardant aconitic acid-derived monomers 704, according to some embodiments of the present disclosure. Each monomer 704 has two phenyl (Ph)-substituted FR groups. In processes 700-1 and 700-2, the phenol-functionalized aconitic acid derivative 464 is converted to a mono-allyl-functionalized di-Ph-FR flame-retardant aconitic acid-derived monomer 704-1 and a mono-epoxy-functionalized di-Ph-FR flame-retardant aconitic acid-derived monomer 704-2, respectively. In process 700-3, the mono-epoxy-functionalized di-Ph-FR flame-retardant aconitic acid-derived monomer 704-2 is converted to a mono-propylene carbonate-functionalized di-Ph-FR flame-retardant aconitic acid-derived monomer 704-3. Processes 700-1, 700-2, and 700-3 are carried out under substantially the same conditions as processes 500-1, 500-2, and 500-3, respectively.

Figure 7B:
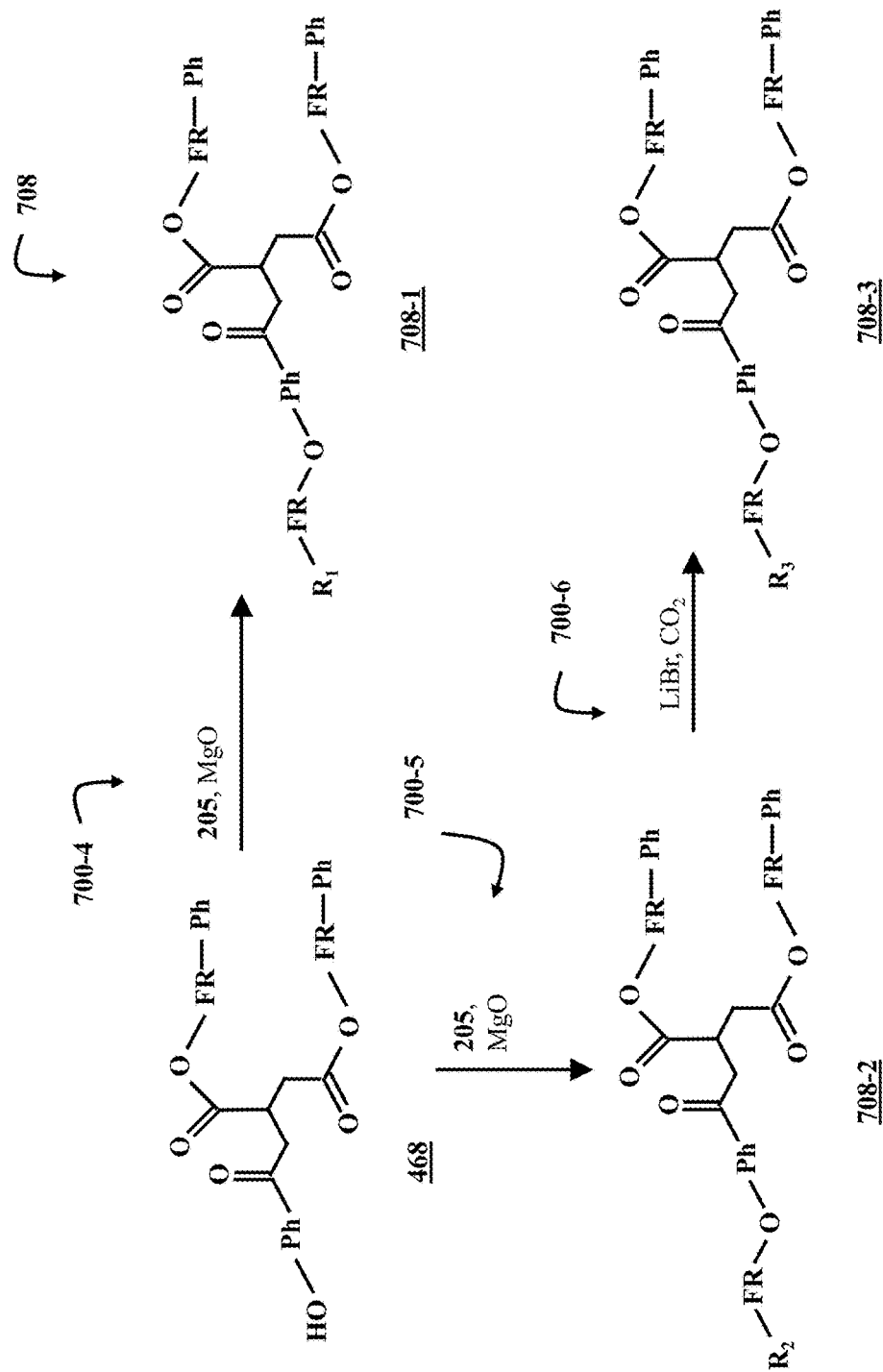
FIG. 7B is a chemical reaction diagram illustrating processes of forming mono-functionalized di-Ph-FR flame-retardant carboxysuccinic acid-derived monomers, according to some embodiments of the present disclosure.

FIG. 7B is a chemical reaction diagram illustrating processes 700-4, 700-5, and 700-6 of forming mono-functionalized di-Ph-FR flame-retardant carboxysuccinic acid-derived monomers 708, according to some embodiments of the present disclosure. Each monomer 708 has two phenyl (Ph)-substituted FR groups. In processes 700-4 and 700-5, the phenol-functionalized carboxysuccinic acid derivative 468 is converted to a mono-allyl-functionalized di-Ph-FR flame-retardant carboxysuccinic acid-derived monomer 708-1 and a mono-epoxy-functionalized di-Ph-FR flame-retardant carboxysuccinic acid-derived monomer 708-2, respectively. In process 700-6, the mono-epoxy-functionalized di-Ph-FR flame-retardant carboxysuccinic acid-derived monomer 708-2 is converted to a mono-propylene carbonate-functionalized di-Ph-FR flame-retardant carboxysuccinic acid-derived monomer 708-3. Processes 700-4, 700-5, and 700-6 are carried out under substantially the same conditions as processes 500-1, 500-2, and 500-3, respectively.

Figure 7C:
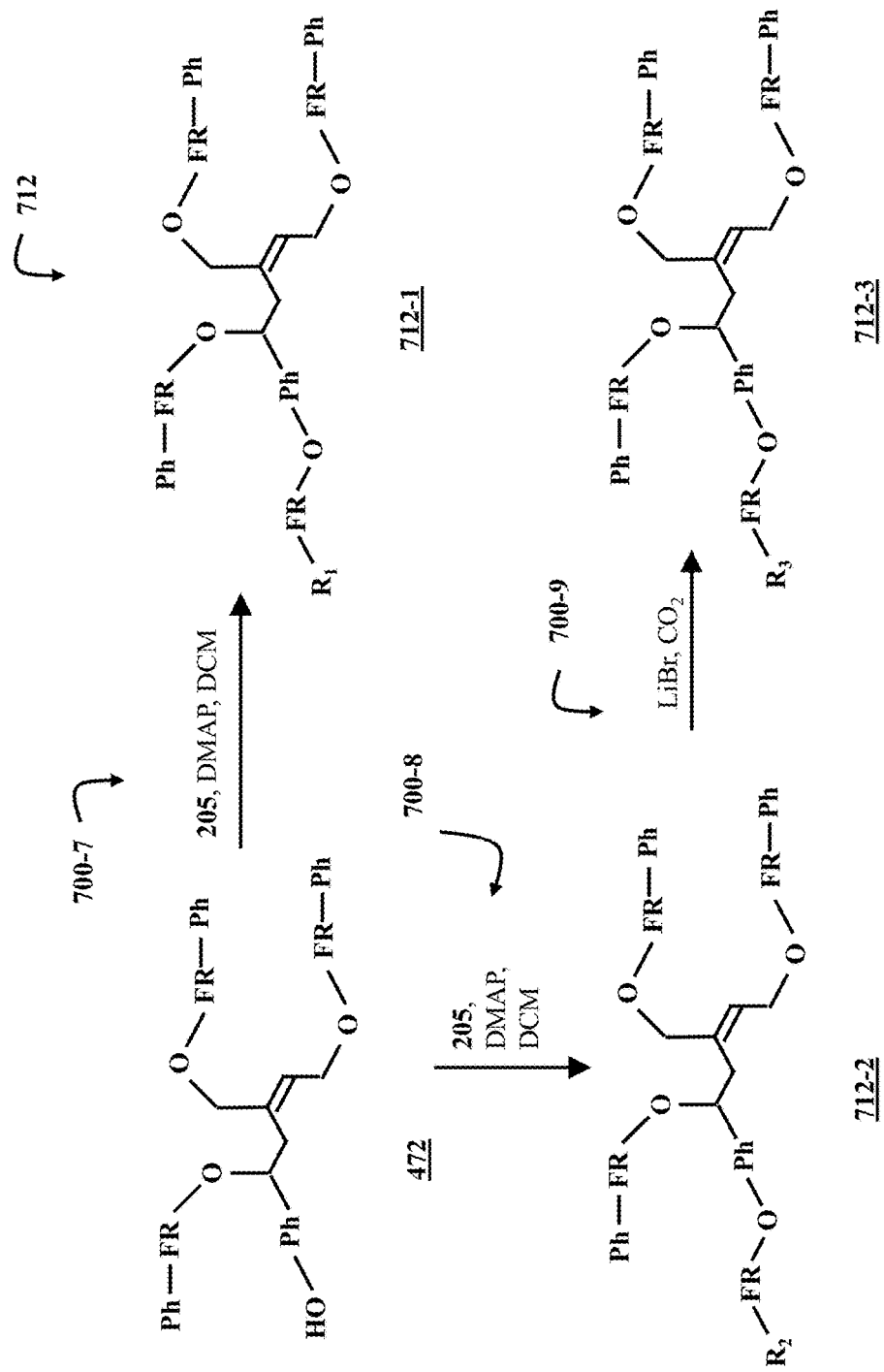
FIG. 7C is a chemical reaction diagram illustrating processes of forming mono-functionalized tri-Ph-FR flame-retardant butenetriol-derived monomers, according to some embodiments of the present disclosure.

FIG. 7C is a chemical reaction diagram illustrating processes 700-7, 700-8, and 700-9 of forming mono-functionalized tri-Ph-FR flame-retardant butenetriol-derived monomers 712, according to some embodiments of the present disclosure. Each monomer 712 has three phenyl (Ph)-substituted FR groups. In processes 700-7 and 700-8, the phenol-functionalized butenetriol derivative 472 is converted to a mono-allyl-functionalized di-Ph-FR flame-retardant butenetriol-derived monomer 712-1 and a mono-epoxy-functionalized di-Ph-FR flame-retardant butenetriol-derived monomer 712-2, respectively. In process 700-9, the mono-epoxy-functionalized di-Ph-FR flame-retardant butenetriol-derived monomer 712-2 is converted to a mono-propylene carbonate-functionalized di-Ph-FR flame-retardant butenetriol-derived monomer 712-3. Processes 700-7, 700-8, and 700-9 are carried out under substantially the same conditions as processes 500-13, 500-14, and 500-15, respectively. Processes 500-13, 500-14, and 500-15, are discussed in greater detail with regard to FIG. 5E.

Figure 7D:
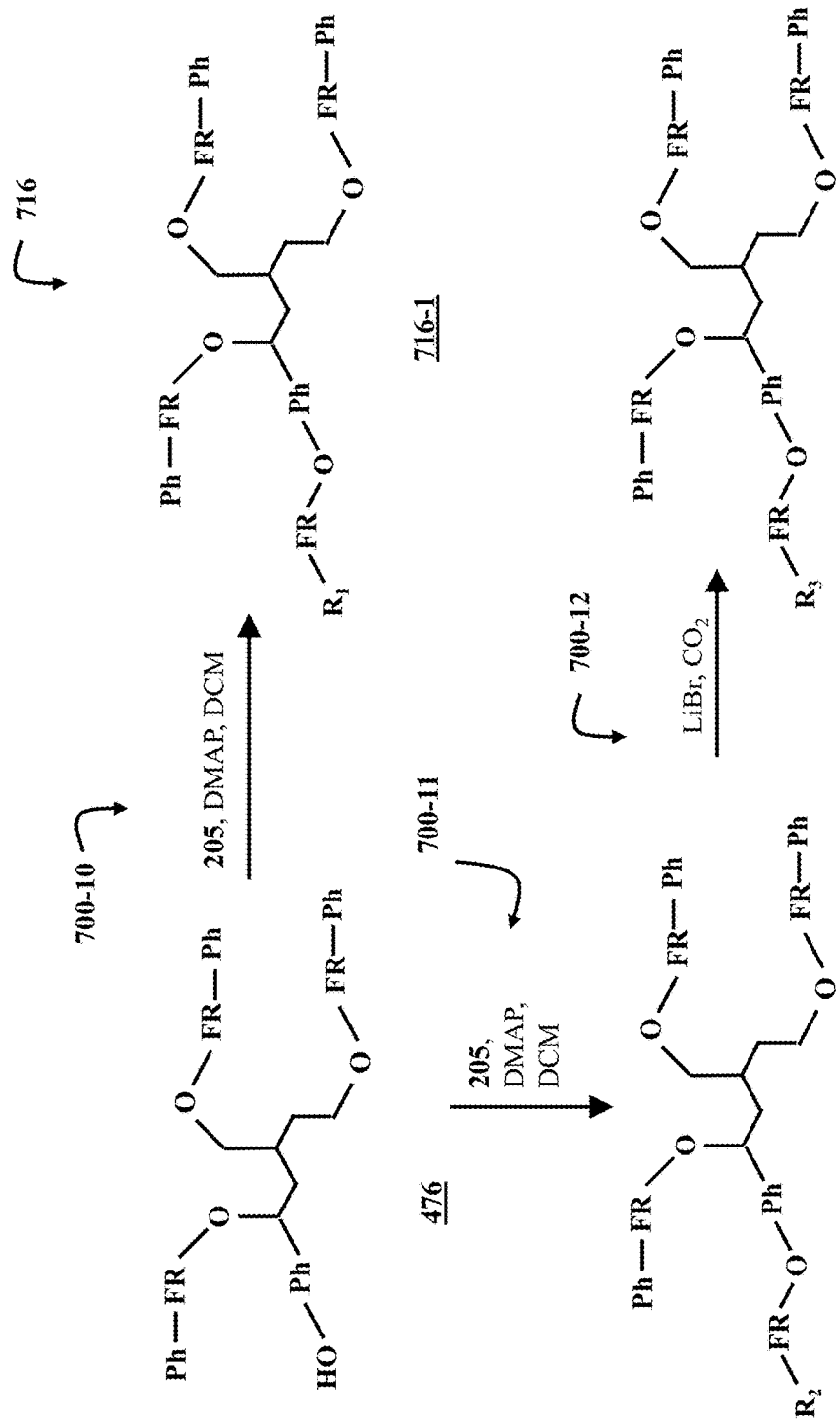
FIG. 7D is a chemical reaction diagram illustrating processes of forming mono-functionalized tri-Ph-FR flame-retardant butanetriol-derived monomers, according to some embodiments of the present disclosure.

FIG. 7D is a chemical reaction diagram illustrating processes 700-10, 700-11, and 700-12 of forming mono-functionalized tri-Ph-FR flame-retardant butanetriol-derived monomers 716, according to some embodiments of the present disclosure. Each monomer 716 has three phenyl (Ph)-substituted FR groups. In processes 700-10 and 700-11, the phenol-functionalized butanetriol derivative 476 is converted to a mono-allyl-functionalized tri-Ph-FR flame-retardant butanetriol-derived monomer 716-1 and a mono-epoxy-functionalized tri-Ph-FR flame-retardant butanetriol-derived monomer 716-2, respectively. In process 700-12, the mono-epoxy-functionalized tri-Ph-FR flame-retardant butanetriol-derived monomer 716-2 is converted to a mono-propylene carbonate-functionalized tri-Ph-FR flame-retardant butanetriol-derived monomer 716-3. Processes 700-10, 700-11, and 700-12 are carried out under substantially the same conditions as processes 500-13, 500-14, and 500-15, respectively.

The processes of forming the functionalized flame-retardant aconitic acid-derived monomers illustrated in FIGS. 4B, 4G, 4H, 5A-5F, 6A-6F, and 7A-7D can be carried out with different combinations of phosphorus-based flame-retardant molecules 205 and 207. In some embodiments, these processes can be carried out with either all phosphate-based flame-retardant molecules (207-1 or 205-1) or all phosphonate-based flame-retardant molecules (207-2 or 205-2). In other embodiments, a mixture of both phosphate-phosphonate-based flame-retardant molecules can be used. Carrying out these processes with a mixture of phosphate- and phosphonate-based molecules (207-1/207-2 or 205-1/205-2) can result in the production of flame-retardant aconitic acid-derived monomers with both phosphoryl and phosphonyl FR groups.

However, in some instances, adding a mixture of phosphate- and phosphonate-based molecules (207-1/207-2 or 205-1/205-2) can result in the production of flame-retardant aconitic acid-derived monomers with all phosphoryl or all phosphonyl FR moieties. Additionally, adding a mixture of phosphate- and phosphonate-based molecules (207-1/207-2 or 205-1/205-2) to the reaction can yield a mixture of products that includes some combination of flame-retardant aconitic acid-derived monomers with either all phosphoryl or all phosphonyl FR groups and flame-retardant aconitic acid-derived monomers with both phosphoryl and phosphonyl FR groups.

Figure 8A:
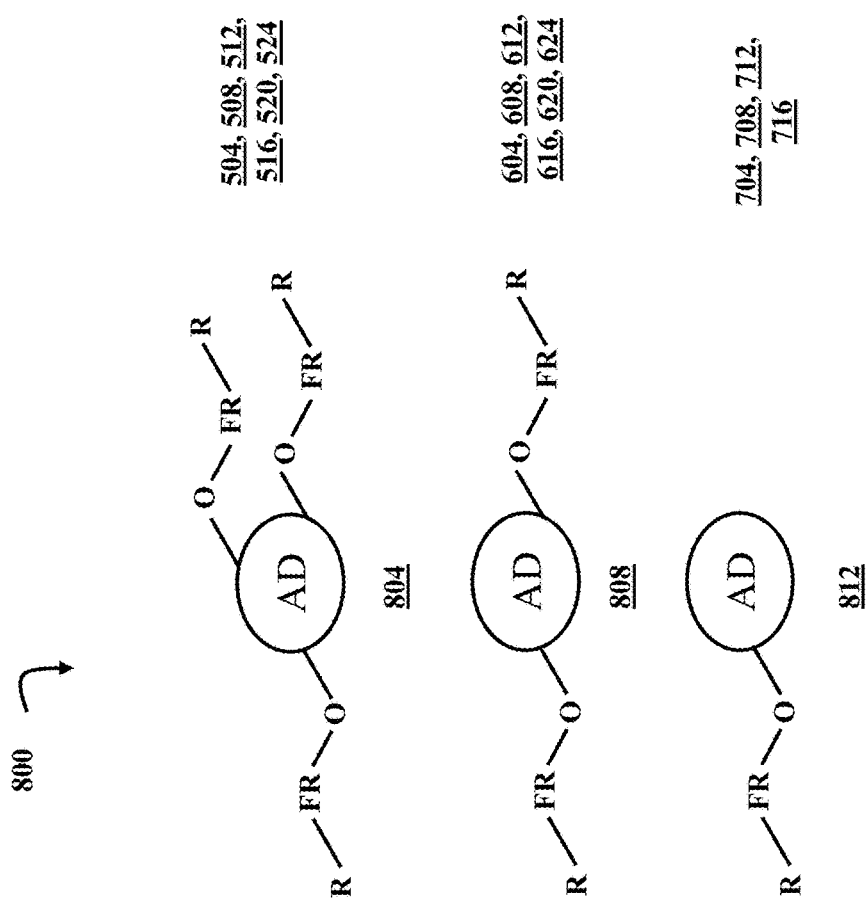
FIG. 8A is a diagrammatic representation of the structures of generic flame-retardant aconitic acid-derived monomers, according to some embodiments of the present disclosure.

FIG. 8A is a diagrammatic representation of the structures 800 of generic flame-retardant aconitic acid-derived monomers, according to some embodiments of the present disclosure. The monomers are tri-functionalized flame-retardant aconitic acid-derived monomers 804, di-functionalized flame-retardant aconitic acid-derived monomers 808, and mono-functionalized flame-retardant aconitic acid-derived monomers 812. Each structure shows only the ligands with R functional groups (i.e., allyl, epoxy, or propylene carbonate). An oval labeled "AD" represents the aconitic acid-derivative core of each monomer. Because the aconitic acid-derivative core is variable, the tri-functionalized flame-retardant aconitic acid-derived monomers 804 can be any of the tri-functionalized flame-retardant monomers 504, 508, 512, 516, 520, and 524. Likewise, the di-functionalized aconitic acid-derived monomers 808 can be any of the di-functionalized flame-retardant monomers 604, 608, 612, 616, 620, and 624. Further, the mono-functionalized aconitic acid-derived monomers 812 can be any of the mono-functionalized flame-retardant monomers 704, 708, 712, and 716.

Figure 8B:
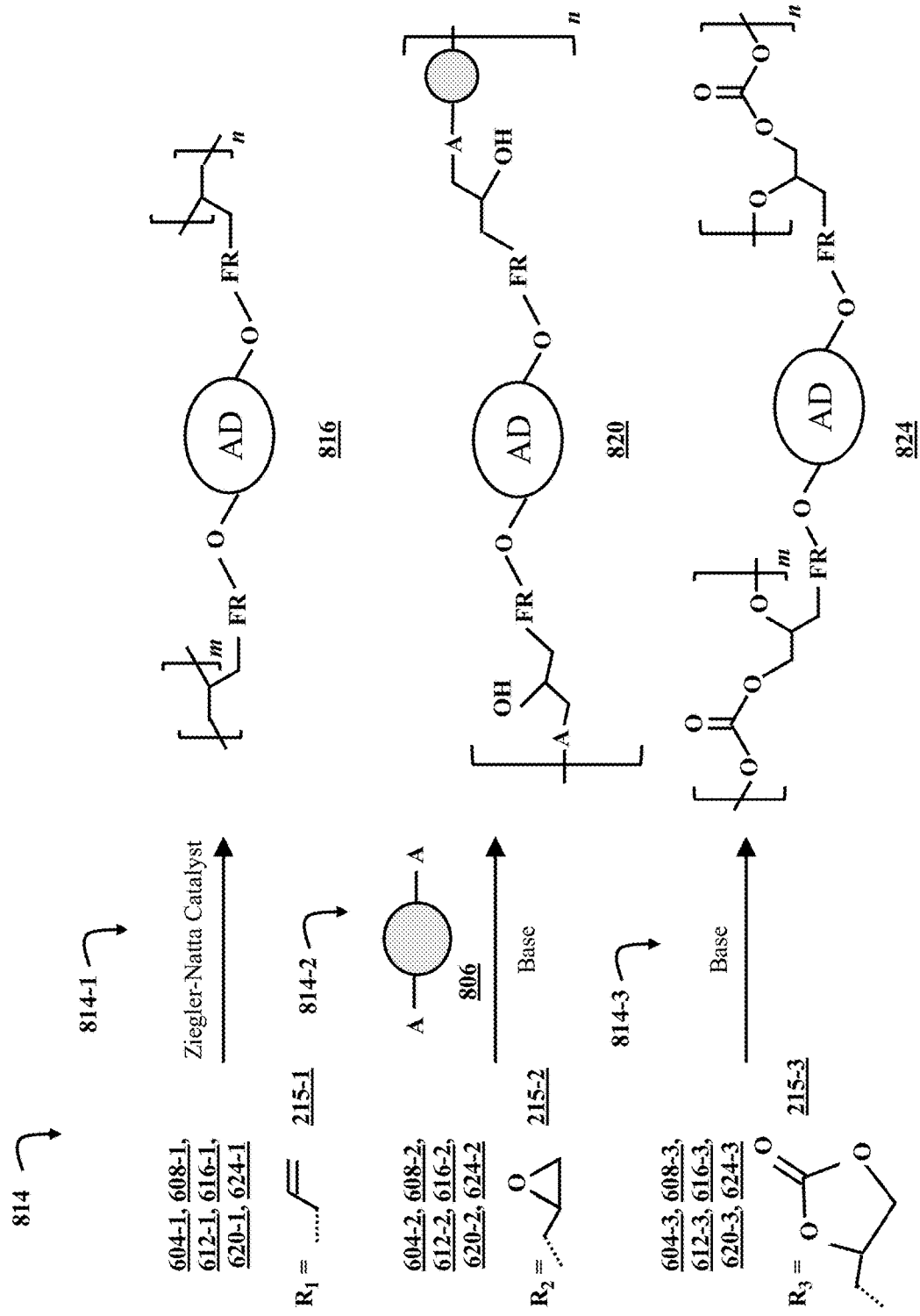
FIG. 8B is a chemical reaction diagram illustrating processes of synthesizing flame-retardant aconitic acid-based polymers from flame-retardant aconitic acid-derived monomers, according to some embodiments of the present disclosure.

FIG. 8B is a chemical reaction diagram illustrating processes 814 of synthesizing flame-retardant aconitic acid-based polymers 816, 820, and 824 from flame-retardant aconitic acid-derived monomers, according to some embodiments of the present disclosure. The reactions illustrated herein are prophetic examples of polymers that can be synthesized from the flame-retardant aconitic acid-derived monomers, but other polymers can be produced as well (e.g., by changing reaction conditions, co-monomers, R groups, etc.).

Processes 814-1-814-3 illustrate the polymerization of di-functionalized flame-retardant aconitic acid-derived monomers 808 only. However, it should be noted that each of these polymerization reactions can also be carried out with the tri-functionalized flame-retardant aconitic acid-derived monomers 804. Additionally, processes 814-1 and 814-3 can be carried out with the mono-functionalized flame-retardant aconitic acid-derived monomers 812. Further, in some embodiments, the polymerization reactions are carried out with a combination of both di-functionalized flame-retardant aconitic acid-derived monomers 808 and tri-functionalized flame-retardant aconitic acid-derived monomers 804, both di-functionalized flame-retardant aconitic acid-derived monomers 808 and mono-functionalized flame-retardant aconitic acid-derived monomers 812, both tri-functionalized flame-retardant aconitic acid-derived monomers 804 and mono-functionalized flame-retardant aconitic acid-derived monomers 812, or a combination of monomers that includes tri-, di-, and mono-functionalized monomers in any ratio.

In process 814-1, allyl-derived flame-retardant aconitic acid-based polymers 816 are formed from di-allyl-functionalized flame-retardant aconitic acid-derived monomers 604-1, 608-1, 612-1, 616-1, 620-1, and 624-1. The di-allyl-functionalized flame-retardant aconitic acid-derived monomer 604-1, 608-1, 612-1, 616-1, 620-1, or 624-1 is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 814-2, epoxy-derived flame-retardant aconitic acid-based polymers 820 are formed from di-epoxy functionalized flame-retardant aconitic acid-derived monomers 604-2, 608-2, 612-2, 616-2, 620-2, and 624-2. The di-epoxy-functionalized flame-retardant aconitic acid-derived monomer 604-2, 608-2, 612-2, 616-2, 620-2, or 624-2 is reacted with a base and a second monomer 806. The second monomer 806 is a compound with at least two hydroxyl (OH) groups or at least two amino ($NH_2$) groups (e.g., a diol, polyol, diamine, polyamine, etc.) 806. These compounds 806 are illustrated as a gray oval with attached A groups. The A group represents a hydroxyl group or an amino group. It should be noted that, while two A groups are illustrated herein, there are more than two A groups in some embodiments. Additionally, in some embodiments, the di-epoxy-functionalized aconitic acid-derived monomer 604-2, 608-2, 612-2, 616-2, 620-2, or 624-2 self-polymerizes under basic conditions. In these instances, the reaction does not include the second monomer 806.

In process 814-3, propylene carbonate-derived flame-retardant aconitic acid-based polymers 824 are formed from di-propylene carbonate-functionalized flame-retardant aconitic acid-derived monomers 604-3, 608-3, 612-3, 616-3, 620-3, and 624-3. The di-propylene carbonate-functionalized flame-retardant aconitic acid-derived monomer 604-3, 608-3, 612-3, 616-3, 620-3, or 624-3 is reacted in a ring-opening polymerization initiated by a base. Examples of bases that can be used as initiators can include potassium hydroxide (KOH), sodium hydroxide (NaOH), lithium hydroxide (LiOH), etc.

In addition to the polymers illustrated in FIG. 8B, the flame-retardant aconitic acid-derived monomers disclosed herein can be used in the synthesis of other flame-retardant polymers, in some embodiments. An array of classes of flame-retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, polycarbonates, epoxy resins, polyimides, polyureas, polyamides, poly(vinyl-esters), etc.

One example of an application of polymers made, at least in part, from flame-retardant aconitic acid-derived monomers is in plastics used in electronics hardware. Additional applications can include acoustic dampening, cushioning, plastics, synthetic fibers, insulation, etc. The flame-retardant aconitic acid-derived monomers can also be used to make adhesives such as bio-adhesives, elastomers, thermoplastics, emulsions, thermosets, etc. Further, materials containing the flame-retardant aconitic acid-derived monomers can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating polymers that are made, at least in part, from aconitic acid-based flame-retardant monomers. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the flame-retardant aconitic acid-derived monomers can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame-retardant aconitic acid-derived monomer comprising:
    at least one phosphorus-based moiety; and
    at least one functional group selected from a group consisting of an allyl functional group, an epoxy functional group, and a propylene carbonate functional group, wherein the at least one functional group participates in a polymerization reaction.

2. The flame-retardant aconitic acid-derived monomer of claim 1, wherein the flame-retardant aconitic acid-derived monomer is selected from a group of tri-functionalized flame-retardant aconitic acid-derived monomers with formulas of:

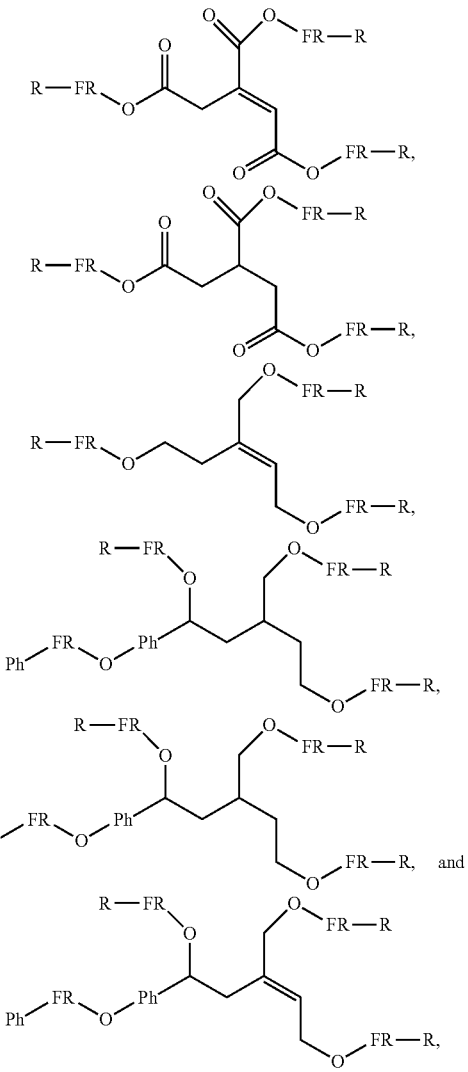

wherein FR is the at least one phosphorus-based moiety; and
wherein R is the functional group selected from the group consisting of the allyl functional group, the epoxy functional group, and the propylene carbonate functional group.

3. The flame-retardant aconitic acid-derived monomer of claim 1, wherein the flame-retardant aconitic acid-derived monomer is selected from a group of di-functionalized flame-retardant aconitic acid-derived monomers with formulas of:

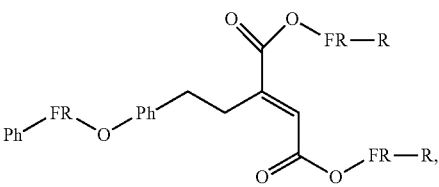

-continued

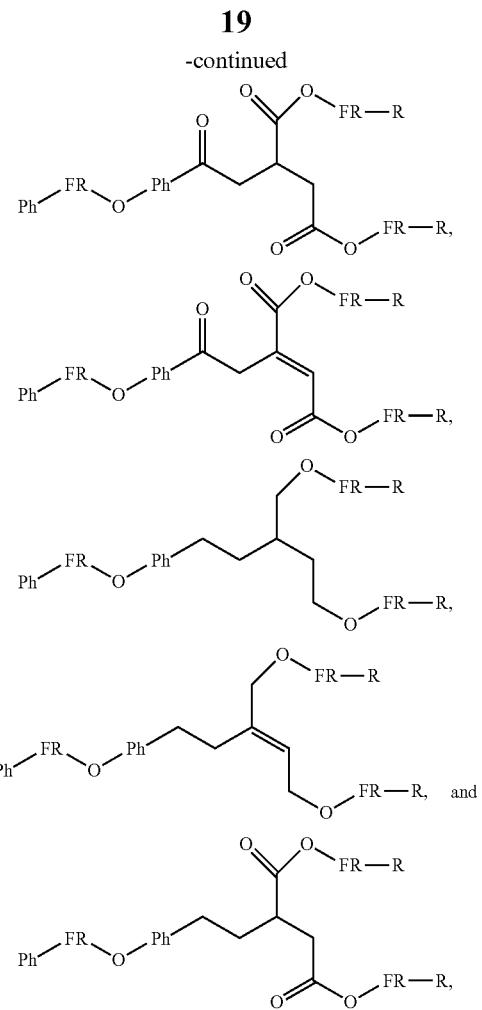

wherein FR is the at least one phosphorus-based moiety; and wherein R is the functional group selected from the group consisting of the allyl functional group, the epoxy functional group, and the propylene carbonate functional group.

4. The flame-retardant aconitic acid-derived monomer of claim 1, wherein the flame-retardant aconitic acid-derived monomer is selected from a group of mono-functionalized flame-retardant aconitic acid-derived monomers with formulas of:

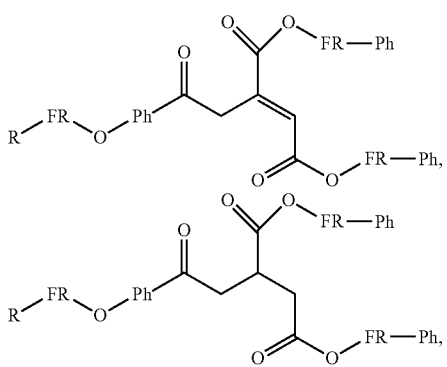

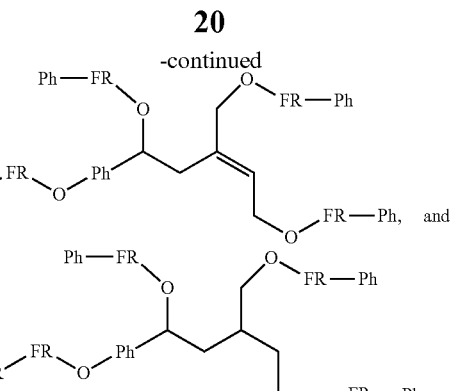

wherein FR is the at least one phosphorus-based moiety; and wherein R is the functional group selected from the group consisting of the allyl functional group, the epoxy functional group, and the propylene carbonate functional group.

5. The flame-retardant aconitic acid-derived monomer of claim 1, wherein the at least one phosphorus-based moiety is a phosphoryl moiety with a formula of:

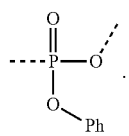

6. The flame-retardant aconitic acid-derived monomer of claim 1, wherein the at least one phosphorus-based moiety is a phosphonyl moiety with a formula of:

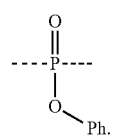

7. A process of forming a flame-retardant polymer, comprising:
   forming a phosphorus-based flame-retardant molecule;
   forming an aconitic acid derivative;
   chemically reacting the aconitic acid derivative with the phosphorus-based flame-retardant molecule to form an aconitic acid-based flame-retardant monomer; and
   polymerizing the flame-retardant aconitic acid-derived monomer.

8. The process of claim 7, wherein the aconitic acid derivative is synthesized from aconitic acid that has been obtained from a bio-based source.

9. The process of claim 8, wherein the bio-based source is citric acid.

10. The process of claim 7, wherein the flame-retardant aconitic acid-derived monomer is polymerized in a polymerization reaction with a basic reagent.

11. The process of claim 7, wherein the flame-retardant aconitic acid-derived monomer is polymerized in a reaction between the flame-retardant aconitic acid-derived monomer and a second monomer with at least two hydroxyl groups.

12. The process of claim 7, wherein the flame-retardant aconitic acid-derived monomer is polymerized in a reaction between the flame-retardant aconitic acid-derived monomer and a second monomer with at least two amino groups.

13. The process of claim 7, wherein the flame-retardant aconitic acid-derived monomer is polymerized in a reaction with a Ziegler-Natta catalyst.

14. The process of claim 7, wherein the phosphorus-based flame-retardant molecule is selected from a group consisting of phosphorus-based molecules with formulas of:

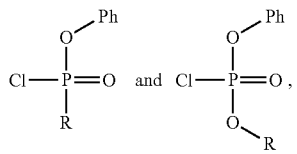

wherein R is selected from a group consisting of an allyl functional group and an epoxy functional group.

15. An article of manufacture, comprising:
a material containing a flame-retardant aconitic acid-derived polymer formed from a polymerization of a flame-retardant aconitic acid-derived monomer, the monomer comprising:
at least one phosphorus-based moiety; and
at least one functional group, wherein the at least one functional group participates in the polymerization reaction.

16. The article of manufacture of claim 15, further comprising an electronic component.

17. The article of manufacture of claim 15, wherein the material is a plastic.

18. The article of manufacture of claim 15, wherein the material is an adhesive.

* * * * *